US009913957B2

(12) United States Patent
Gongmin et al.

(10) Patent No.: US 9,913,957 B2
(45) Date of Patent: Mar. 13, 2018

(54) POWER SWITCH FOR AUXILIARY COMMON GAS OUTLET

(71) Applicant: Mindray DS USA, Inc., Mahwah, NJ (US)

(72) Inventors: Wang Gongmin, Shenzhen (CN); Geoffrey C. Jawidzik, Mahwah, NJ (US); Xiong Zhibin, Shenzhen (CN); Chen Peitao, Shenzhen (CN); Cai Kun, Shenzhen (CN)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 1413 days.

(21) Appl. No.: 13/705,473

(22) Filed: Dec. 5, 2012

(65) Prior Publication Data

US 2014/0150786 A1 Jun. 5, 2014

(51) Int. Cl.
*A61M 15/00* (2006.01)
*A61M 16/20* (2006.01)
(Continued)

(52) U.S. Cl.
CPC ........ *A61M 16/20* (2013.01); *A61M 16/0051* (2013.01); *A61M 16/104* (2013.01);
(Continued)

(58) Field of Classification Search
CPC ................ A47C 27/081; A47C 27/10; A61M 2016/0027; A61M 2016/0033;
(Continued)

(56) References Cited

U.S. PATENT DOCUMENTS 3,114,365 A * 12/1963 Franz .................... A61M 16/00
128/204.19
3,754,550 A * 8/1973 Kipling ................. A61M 16/00
128/205.16
(Continued)

FOREIGN PATENT DOCUMENTS

EP 2236876 A2 10/2010

OTHER PUBLICATIONS

International Search Report and Written Opinion for PCT/US2013/070128 filed Nov. 14, 2013, dated Feb. 27, 2014.
(Continued)

*Primary Examiner* — Todd J Scherbel
*Assistant Examiner* — Victoria Murphy
(74) *Attorney, Agent, or Firm* — Kory D. Christensen; Polsinelli LLP

(57) ABSTRACT

In various embodiments, flow rate of fluids, such as oxygen, nitrous oxide, and air, may be electronically and/or mechanically controlled. An electronically controlled auxiliary common gas output (ACGO) valve may direct the gas mixture, including one or more gases and/or anesthetics, either to a primary breathing machine or to an ACGO of an anesthesia delivery machine. The ACGO valve may include a piloted shuttle valve comprising a valve body and a piston configured to translate within the valve body. The piston may divert the gas mixture to a primary breathing system outlet when translated to a first position and to an ACGO when translated to a second position. An electronically controlled drive gas may toggle the position of the piston. In some embodiments, the piloted shuttle valve may be spring loaded and default to directing the gas mixture to the primary breathing system.

24 Claims, 17 Drawing Sheets

(51) Int. Cl.
*A61M 16/00* (2006.01)
*A61M 16/10* (2006.01)
*A61M 16/12* (2006.01)
*A61M 16/18* (2006.01)

(52) U.S. Cl.
CPC .......... *A61M 16/12* (2013.01); *A61M 16/202* (2014.02); *A61M 16/18* (2013.01); *A61M 16/203* (2014.02); *A61M 16/209* (2014.02); *A61M 2016/0027* (2013.01); *A61M 2016/0033* (2013.01); *A61M 2202/0208* (2013.01); *A61M 2202/0283* (2013.01); *A61M 2205/3334* (2013.01); *A61M 2205/50* (2013.01); *A61M 2205/505* (2013.01); *A61M 2205/8206* (2013.01); *A61M 2209/084* (2013.01)

(58) Field of Classification Search
CPC ............ A61M 16/0051; A61M 16/104; A61M 16/12; A61M 16/18; A61M 16/20; A61M 16/201; A61M 16/202; A61M 16/203; A61M 16/209; A61M 2202/0208; A61M 2202/0283; A61M 2205/3334; A61M 2205/50; A61M 2205/505; A61M 2205/8206; A61M 2209/084; A61M 16/01; A61M 16/021; B64G 1/26; B64G 1/401; B64G 1/402; C02F 1/42; F15B 11/006; F15B 2211/30575; F15B 2211/329; F15B 2211/7052; F15B 13/0402; F15B 13/0405; F15B 13/0431; F15C 3/00; F16K 11/00; F16K 11/065; F16K 11/0655; F16K 11/07; F16K 11/0712; F16K 11/24; F16K 31/082; F16K 31/122; F16K 31/1225; F16K 31/1635; F16K 31/363
USPC ............... 137/554, 625.48, 869, 872; 251/31
See application file for complete search history.

(56) References Cited

U.S. PATENT DOCUMENTS

| | | | | |
|---|---|---|---|---|
| 3,850,170 | A * | 11/1974 | Cox | A61M 16/00 128/204.24 |
| 4,227,519 | A * | 10/1980 | Warnow | A61M 16/00 128/205.24 |
| 4,705,034 | A * | 11/1987 | Perkins | A61M 16/00 128/204.21 |
| 4,823,840 | A * | 4/1989 | Kosugi | F16K 11/044 137/625.27 |
| 4,832,014 | A * | 5/1989 | Perkins | A61M 16/00 128/203.12 |
| 5,038,827 | A | 8/1991 | Heffner et al. | |
| 5,095,941 | A * | 3/1992 | Betz | E03C 1/052 137/552 |
| 5,511,763 | A * | 4/1996 | Green | E03C 1/052 251/129.02 |
| 5,513,790 | A * | 5/1996 | Giusto | B21D 43/11 137/625.66 |
| 5,558,083 | A * | 9/1996 | Bathe | A61M 16/12 128/203.12 |
| 5,887,611 | A | 5/1999 | Lampotang et al. | |
| 6,250,302 | B1 * | 6/2001 | Rantala | A61M 16/00 128/204.21 |
| 6,305,372 | B1 | 10/2001 | Servidio | |
| 6,427,720 | B1 * | 8/2002 | Hayashi | F15B 13/0402 137/554 |
| 7,073,502 | B2 * | 7/2006 | Bromster | A61M 16/08 128/205.13 |
| 7,992,555 | B2 * | 8/2011 | Heinonen | A61M 16/01 128/204.21 |
| 8,424,523 | B2 * | 4/2013 | Ogilvie | A61M 16/12 128/204.22 |
| 8,453,678 | B2 * | 6/2013 | Neff | F16K 11/07 137/625.27 |
| 8,464,753 | B2 * | 6/2013 | Schmidt | F15B 11/006 137/596.14 |
| 2004/0163706 | A1 | 8/2004 | Volgyesi | |
| 2005/0087243 | A1 | 4/2005 | Shaw et al. | |
| 2008/0054204 | A1 | 3/2008 | Zhou | |
| 2009/0126734 | A1 | 5/2009 | Dunsmore et al. | |
| 2010/0224191 | A1 | 9/2010 | Dixon et al. | |
| 2010/0252046 | A1 | 10/2010 | Dahlstrom et al. | |
| 2010/0252132 | A1 * | 10/2010 | Neff | F16K 11/07 137/625.17 |

OTHER PUBLICATIONS

International Preliminary Report on Patentability for PCT/US2013/070128 filed Nov. 14, 2013, dated May 28, 2015.
International Search Report and Written Opinion for PCT/US2013/073183 filed Dec. 4, 2013, dated Mar. 3, 2014.
International Preliminary Report on Patentability for PCT/US2013/073183 filed Dec. 4, 2013, dated Jun. 9, 2015.

* cited by examiner

State 1

State 2

State 1

State 2 ly to function as manual flow controls in the event of a power loss or other electronic failure.

POWER SWITCH FOR AUXILIARY COMMON GAS OUTLET

TECHNICAL FIELD

This disclosure relates generally to controlling the flow of fluids in an anesthesia delivery system. Particularly, this disclosure relates to electronically diverting the flow of gas from a primary breathing system to an auxiliary system.

SUMMARY

In various embodiments, a practitioner may control the flow rate of fluids (gases and/or liquids), such as oxygen, nitrous oxide, and air, in modern anesthesia delivery systems electronically and/or mechanically. One or more control knobs may be configured to electronically or mechanically control a flow rate of one or more gases. An anesthesia delivery system may utilize manual controls as the primary control system for controlling the flow rates of one or more gases and/or anesthetics. Alternatively, manual controls may be configured as backup controls to an electronic system.

The gas mixture, including one or more gases and/or anesthetics, may be directed to a patient via a primary breathing machine. The primary breathing machine may include any type of breathing system, such as non-rebreathers, closed circuit rebreathers, and semi-closed circuit rebreathers. The gas mixture may alternatively and/or additionally be directed to a patient via an auxiliary breathing machine. For example, an anesthesia delivery system may include an auxiliary common gas output. The gas mixture may be directed to the auxiliary common gas output, where it may be fed into an auxiliary breathing machine or other gas system.

In some embodiments, the gas mixture may be selectively directed toward either the primary breathing system or the auxiliary common gas output. In one embodiment, the gas mixture is diverted through the use of a manual operated pneumatic control or switch. For example, switching from the primary breathing system to an auxiliary breathing system may be accomplished using a manually actuated pneumatic selector valve.

In other embodiments, an electronically controlled auxiliary common gas output (ACGO) valve may be configured to selectively direct the gas mixture to either a primary breathing system or an ACGO. For example, the switching may be controlled via an electronic button, switch, dial, slider, touch screen, or other electronic input. The ACGO valve may be configured to accommodate relatively high flow rates of one or more gases and/or anesthetics, provide biocompatibility, operate in an oxygen rich environment, and/or convey potentially corrosive anesthetic agents.

Additionally, whereas a mechanically actuated switch remains in a last-used state, the ACGO valve may be configured to revert to a state most likely to be used next. Additionally, in one embodiment, the ACGO valve may be configured to automatically switch the flow of gas from the primary breathing system to an ACGO based on a detected gas connection (e.g., a tube) or electronic connection to an auxiliary output.

As described in detail below, a piloted shuttle valve may selectively direct the flow of a gas mixture between a primary breathing system and an ACGO. The piloted shuttle valve may be toggled between two states by a drive gas (or other drive-fluid). The drive gas may be controlled by one or more latching selector valves. In various embodiments, the latching selector valves are bi-stable. In some embodiments, the one or more latching selector valves may be replaced by any of a wide variety of valves, including those valves that are not bi-stable. The piloted shuttle valve may be configured as a gas-driven bi-stable diversion valve.

Alternatively, the piloted shuttle valve may be configured to direct a gas mixture to a primary breathing system, unless it is driven by a drive gas to direct the gas mixture to an ACGO. For example, the piloted shuttle valve may be spring loaded and default to directing the gas mixture to the primary breathing system. The piloted shuttle valve may include a valve body and a piston configured to translate within the valve body. The valve body may include an inlet for a gas mixture and two outlets for the gas mixture. The piston may divert gas to a primary breathing system outlet when translated to a first position and to an ACGO when translated to a second position.

In one embodiment, the valve body may include a resilient member, such as a spring, on one end of the piston to cause the piston to default to the first position. The valve body may include a drive gas inlet configured to allow a drive gas to selectively drive the piston to the second position. In some embodiments, the valve body may include a second drive gas inlet. In such an embodiment, the piston may be translated between the first and second positions by selectively driving gas in the first and second drive gas inlets.

In one embodiment, a powered switch may include a piloted shuttle valve to selectively divert a gas mixture between a primary breathing system and an ACGO. The piloted switch may include a piston driven by a drive gas between two translational positions. The drive gas may be selectively directed to either end of the piston based on a network of shuttle valves controlled by a three-way selector valve. The three-way selector valve may be a latching, bi-stable selector valve.

The piloted shuttle valve may also include one or more pressure relief valves and/or position detection switches. The piloted shuttle valve may also include guards and/or covers for any of the various components, such as a switch guard to protect a position detection switch. In various examples provided herein, the fluid is described as a gas, such as oxygen, nitrous oxide, and/or air. However, any of a wide variety of liquids and/or gases may be used in conjunction with various embodiments of the systems and methods described herein.

DETAILED DESCRIPTION

Figure 1:
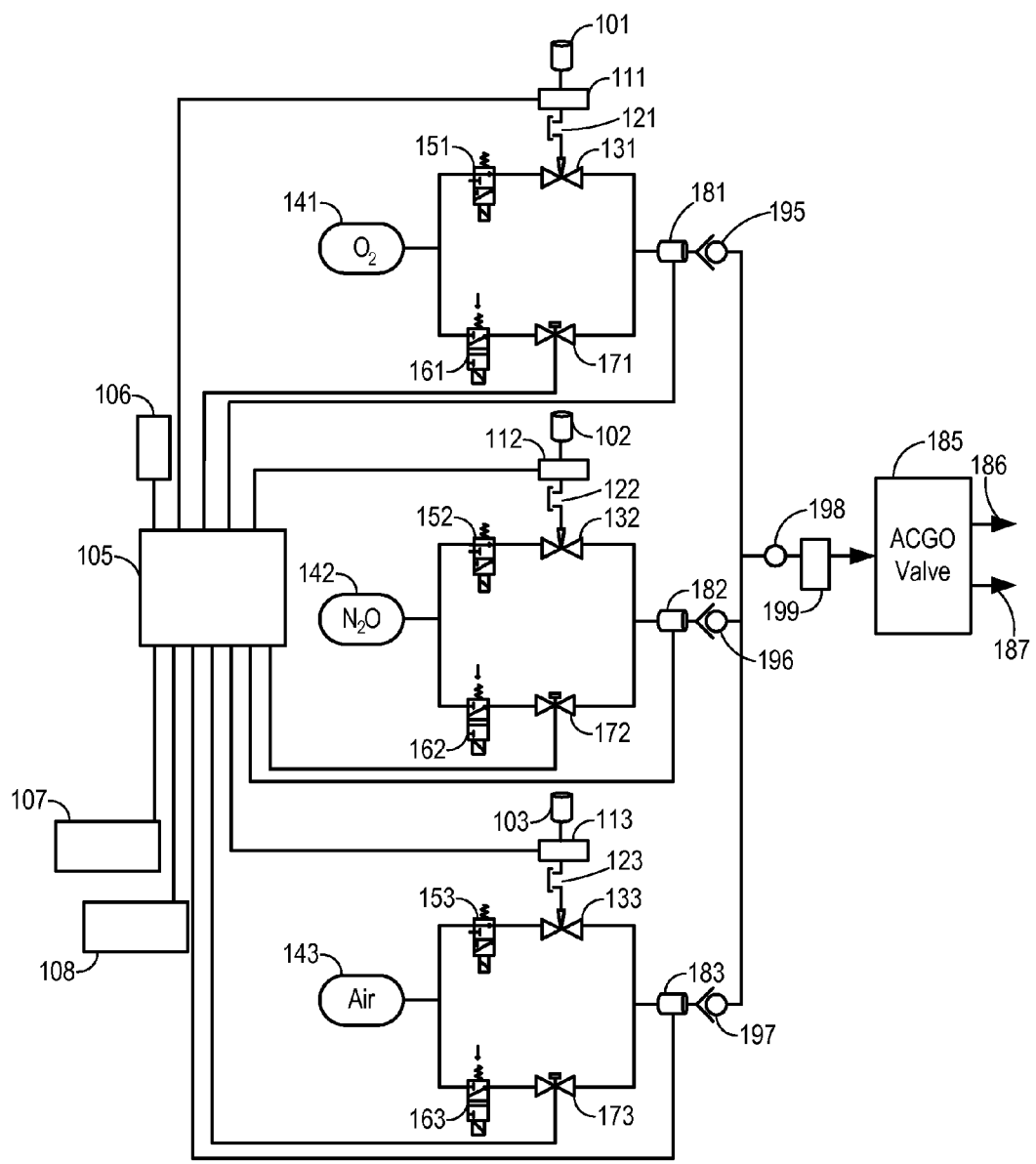
FIG. 1 illustrates a diagram of an anesthesia delivery system in which electronic controls for oxygen, nitrous oxide, and air include manual backup controls.

An electronic flow control valve, such as an electronically controlled proportional valve, may be configured to selectively receive a fluid from a fluid supply. An electronic flow selector may allow a practitioner to select a flow rate of the first fluid via the electronic control valve. From the perspective of the user, the electronic flow selector may be functionally similar to a control knob for a mechanical needle valve. For example, a user may rotate a knob clockwise or counterclockwise in order to decrease or increase the flow rate of a particular fluid. A rotary encoder may electronically encode a selection made via the electronic flow selector and transmit the encoded selection to an electronic controller. The electronic controller may transmit a control signal to the electronic flow control valve to control the flow rate of the fluid based on the selection made via the electronic flow selector.

One or more of the electronic flow selectors may be selectively assignable to control two or more electronic flow control valves. For example, a system may include three electronic flow control valves: one for oxygen, one for air, and one for nitrous oxide. The system may utilize only two electronic flow selectors, one of which may be selectively used to control either the flow rate of the air or the flow rate of the nitrous oxide, and the other assigned to control the flow rate of oxygen. Any electronic flow selector may be permanently assigned or selectively assigned to control the flow rate of any one or more of the available fluids.

While electronic flow control of gases may be useful during anesthesia delivery, it may be desirable to provide manual backup controls as well. For example, in the event of power loss, it may be desirable to continue supplying gases during anesthesia delivery. In some embodiments, electronic controls, such as trim knobs, used in conjunction with encoders, may facilitate the electronic adjustment of the flow rate of one or more gases during anesthesia delivery. Separate backup flow selectors (e.g., knobs) may be available for use in the event of power failure or power unavailability. In such embodiments, the practitioner may need to engage the backup knobs, switch the machine from an electronic mode to a manual mode, and/or ensure that the manual knobs are set to a desirable state prior to switching to a manual mode. In various embodiments, the manual knobs may automatically return to a home state when retracted, such that the flow rate of each of the nitrous oxide, air, and oxygen is automatically set to a default flow rate when the manual knobs are deployed.

Power loss during anesthesia delivery may be confusing and/or disruptive during a critical medical procedure. It may be an inconvenience and/or confusing for a practitioner to see two sets of knobs for controlling the same set of gases. In various embodiments of the present disclosure, flow selectors, such as rotary knobs, may be electronically operable when a fluid flow control system is in a powered state and backup flow selectors may be retracted or otherwise disabled when a fluid flow control system is in a powered state. Confusion may be minimized because the electronic selectors are functionally similar to the manual flow selectors. In an unpowered state, or when a practitioner engages the backup system, the backup flow selectors may be deployed or otherwise enabled.

The number of diversion valve systems, mechanically operated valves, electronically operated valves, controllers, encoders, flow selectors, and/or other components described herein may correspond to the number of gases (or liquids) available. In various anesthesia delivery systems, oxygen, nitrous oxide, and/or air may each be independently controllable and/or proportionally controllable. A mixture of one or more gases may be used in conjunction with a vaporizer to deliver anesthesia.

In one embodiment, a diversion valve system may direct the flow of a gas (or liquid) from a gas supply either to a mechanical flow control valve, such as a mechanically operated needle valve, or to an electronic flow control valve, such as an electronic proportion valve, depending on whether the system has power or a backup system has been engaged.

According to various embodiments, the diversion valve system may include normally-open and normally-closed valves in order to selectively prevent the gas from flowing from (or to) both the mechanically operated needle valve and the electronic proportion valve. The diversion valve system may be implemented using any of a wide variety of valves and/or control systems, such as a three-way selector valve.

In some embodiments, the needle valve may be used as the mechanical flow control valve, and the same needle valve in combination with the electronic stepper motor may be considered the electronic flow control valve. In various embodiments, the flow selector may comprise any of a wide variety of knobs, buttons, rotatable actuators, slides, and/or other analog and/or digital selection devices.

Additionally or alternatively, an on-screen display may allow a user to select the flow rate of one or more gases in either the direct flow control mode or the total flow control mode. An on-screen display may include quick keys for selecting common flow rates of particular gases, a keypad for entering a numeric value associated with a flow rate of one or more gases, digital knobs, digital sliders, up and down arrows, and/or other digitally selectable controls for selecting a flow rate. The electronic selections made via the on-screen display may be transmitted to an electronic controller. The electronic controller may transmit a control signal to the electronic flow control valves to control the flow rate of one or more fluids based on the selections made via the on-screen display.

Once a gas mixture, including one or more gases and/or anesthetics, is selected via electronic and/or manual controls, the gas mixture may be directed to an output. An auxiliary common gas outlet (ACGO) valve may direct the output gas mixture either to a primary breathing system or to an ACGO. The ACGO valve may replace and/or supplement a manually operated pneumatic control switch. The ACGO valve may be configured to accommodate relatively high flow rates of one or more gases and/or anesthetics, provide biocompatibility, operate in an oxygen-rich environment, and/or convey potentially corrosive anesthetic agents.

The primary breathing machine may include any type of breathing system, such as non-rebreathers, closed circuit rebreathers, and semi-closed circuit rebreathers. The ACGO valve may alternatively direct the gas mixture to a patient via an auxiliary breathing machine connected to the ACGO of the anesthesia delivery system. For example, the switching may be controlled via an electronic button, switch, dial, slider, touch screen, or other electronic input.

Additionally, whereas a mechanically actuated switch remains in a last-used state, the electronically controlled ACGO valve may be configured to revert to a state most likely to be used next. For example, the ACGO valve may be configured to automatically switch the flow of gas from the primary breathing system to an auxiliary common gas output, or vice versa, following restart, after power restoration, each time it is used, and/or based on a detected gas connection (e.g., a tube) or electronic connection to an ACGO.

In some embodiments, the ACGO valve may include a piloted shuttle valve. The piloted shuttle valve may selectively direct the flow of a gas mixture between a primary breathing system and the ACGO based on an input drive gas. The drive gas may be controlled by one or more electronically controlled latching selector valves. The latching selector valves may be bi-stable. In some embodiments, the one or more latching selector valves may be replaced by any of a wide variety of valves, including those valves that are not bi-stable.

In some embodiments, the piloted shuttle valve may direct a gas mixture to a primary breathing system in a default state due to a bias from a resilient member, such as a spring or tensioned plate. By directing a drive gas into the piloted shuttle valve, the gas mixture can be switched to flow to the ACGO. The piloted shuttle valve may include a valve body and a piston configured to translate within the valve body. The valve body may include an inlet for a gas mixture and two outlets for the gas mixture. The piston may divert the gas mixture to a primary breathing system outlet when translated to a first position and to an ACGO when translated to a second position. The piston may be biased or default to one of the two positions.

In one embodiment, the valve body may include a resilient member, such as a spring, on one end of the piston to cause the piston to default to the first position. The valve body may include a drive gas inlet configured to allow a drive gas to selectively drive the piston to the second position. In some embodiments, the valve body may include a second drive gas inlet. In such an embodiment, the piston may be translated between the first and second positions by selectively driving gas in the first and second drive gas inlets. In one embodiment, the drive gas may be selectively directed to either end of the piston based on a network of shuttle valves controlled by a three-way selector valve. The three-way selector valve may be a latching, bi-stable selector valve.

The piloted shuttle valve may also include one or more pressure relief valves and/or position detection switches. The piloted shuttle valve may also include guards and/or covers for any of the various components, such as a switch guard to protect a position detection switch.

In various embodiments, a controller or control system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing them in hardware rather than software.

While the various examples and embodiments disclosed herein are described in conjunction with a gas flow control system, many of the embodiments could be used or modified for use with any type of fluid, including various gases and liquids. Gases used for anesthesia delivery, such as oxygen, nitrous oxide, and air, are used herein as examples of gases that can be controlled via the presently described fluid flow control systems, which are referred to as gas flow control systems.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special-purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic storage, optical storage, flash memory, or another machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

FIG. 1 illustrates a diagram of an anesthesia delivery system 100 in which electronic controls for oxygen, nitrous oxide, and air include manual backup control features. A first manually rotatable knob 101 may be used to control the flow rate of a first gas, oxygen 141. A second manually rotatable knob 102 may be used to control the flow rate of a second gas, nitrous oxide 142. A third manually rotatable knob 103 may be used to control the flow rate of a third gas, air 143.

In an electronic mode, the anesthesia delivery system 100 may utilize a controller 105. The controller 105 may implement various functions associated with electronic control of the flow rates of one or more gases, receiving inputs from a practitioner via various peripheral devices, and/or displaying information, such as telemetry data associated with a patient, to a practitioner and/or patient. In some embodiments, electronic control of the flow rates of one or more gases may be implemented via hardware, firmware, and/or software and may be distinct from other electronic controls, microprocessors, and/or the like of the anesthesia delivery system.

In an electronic mode, the anesthesia delivery system 100 may also utilize a touch pad 106 to receive inputs from a practitioner and/or patient. The anesthesia delivery system 100 may also utilize a display 107 and/or associated touch screen 108 when in an electronic mode. Controls may be available to allow the practitioner to control the amount of anesthesia delivered to a patient.

In an electronic mode, a flow rate selection made via one or more of the manually rotatable knobs 101, 102, and 103 may be electronically encoded by an associated encoder 111, 112, and 113. The controller 105 may receive the electronically encoded selection(s) from the encoder(s) 111, 112, and 113. The controller 105 may then transmit corresponding control signals to electronic proportional valves 171, 172, and 173 associated with each of the gases 141, 142, and 143.

In an electronic mode, the normally-closed valves 161, 162, and 163 are opened such that the gases 141, 142, and 143 are allowed to flow to the electronic proportional valves 171, 172, and 173. The normally-open valves 151, 152, and 153 may be closed in an electronic mode to prevent the gases 141, 142, and 143 from flowing through mechanically operated needle valves 131, 132, and 133. Clutches 121, 122, and 123 may disengage the manually rotatable knobs 101, 102, and 103 from the needle valves 131, 132, and 133 to prevent manual adjustment of the needle valves 131, 132, and 133 when the gas flow rate system is in an electronic mode. The gases 141, 142, and 143 may flow through the normally-closed valves 161, 162, and 163 and through the electronic proportion valves 171, 172, and 173 at a flow rate specified by the manually controllable knobs 101, 102, and 103.

In the event power is unavailable, power is lost, an electronic malfunction occurs, and/or a user selects a manual mode, the flow rate of the gases 141, 142, and 143 may be manually controlled by the manually rotatable knobs 101, 102, and 103. In a manual mode, the controller 105, the touchpad 106, the display 107, the touch screen 108, and the encoders 111, 112, and 113 may not function.

According to various embodiments, the manually rotatable knobs 101, 102, and 103 may continue to allow for the uninterrupted control of the flow rate of the gases 141, 142, and 143. The normally-closed valves 161, 162, and 163 may close when the system is in a manual mode. The normally-open valves 151, 152, and 153 may remain in an open state when in a manual mode, allowing gases 141, 142, and 143 to flow to the mechanically operated needle valves 131, 132, and 133. In the manual mode, the clutches 121, 122, and 123 may engage the manually rotatable knobs 101, 102, and 103 with the needle valves 131, 132, and 133, such that the manually rotatable knobs 101, 102, and 103 are operable to manually control the flow of the associated gases 141, 142, and 143 through the needle valves 131, 132, and 133.

Whether electronically controlled in an electronic mode or manually controlled in a manual mode, the flow rate of each gas 141, 142, and 143 may be measured by a flow rate measurement device 181, 182, and 183. Check valves 195, 196, and 197 may prevent backflows of the gases 141, 142, and 143. A total-flow measurement device 198 may measure the combined flow of the gases 141, 142, and 143. A vaporizer 199 may inject one or more anesthetics into the gases 141, 142, and 143.

The output gas mixture, including one or more gases and/or anesthetics, may be directed to an ACGO valve 185. In some embodiments, the ACGO valve 185 may be a manually actuated valve selector operable to selectively direct the gas mixture either to a primary breathing system 186 or to an ACGO 187. The ACGO, for example, may be connected to an auxiliary breathing system. In other embodiments, the ACGO valve 185 may be an electronically controlled valve switch, such as a drive gas controlled piloted shuttle valve, as described in greater detail herein. In some embodiments, the electronically controlled ACGO may be controlled based on electronic inputs and/or signals from the controller 105, the touchpad 106, the display 107, and/or the touch screen 108.

For example, an operator may utilize the touchpad 106, touch screen 108, and/or other electronic input to selectively divert the gas mixture either to the primary breathing system 186 or to the ACGO 187. The electronic signals may actuate and/or toggle a selector valve, such as a bi-stable latching selector valve, to cause a drive gas to toggle the position of a piloted shuttle valve. The piloted shuttle valve may direct the gas mixture to one of two outputs, depending on the position of an internal piston. Numerous examples of electronically controlled valve switches, including piloted shuttle valves, drive gas selector valves, and the like are provided herein.

Figure 2:
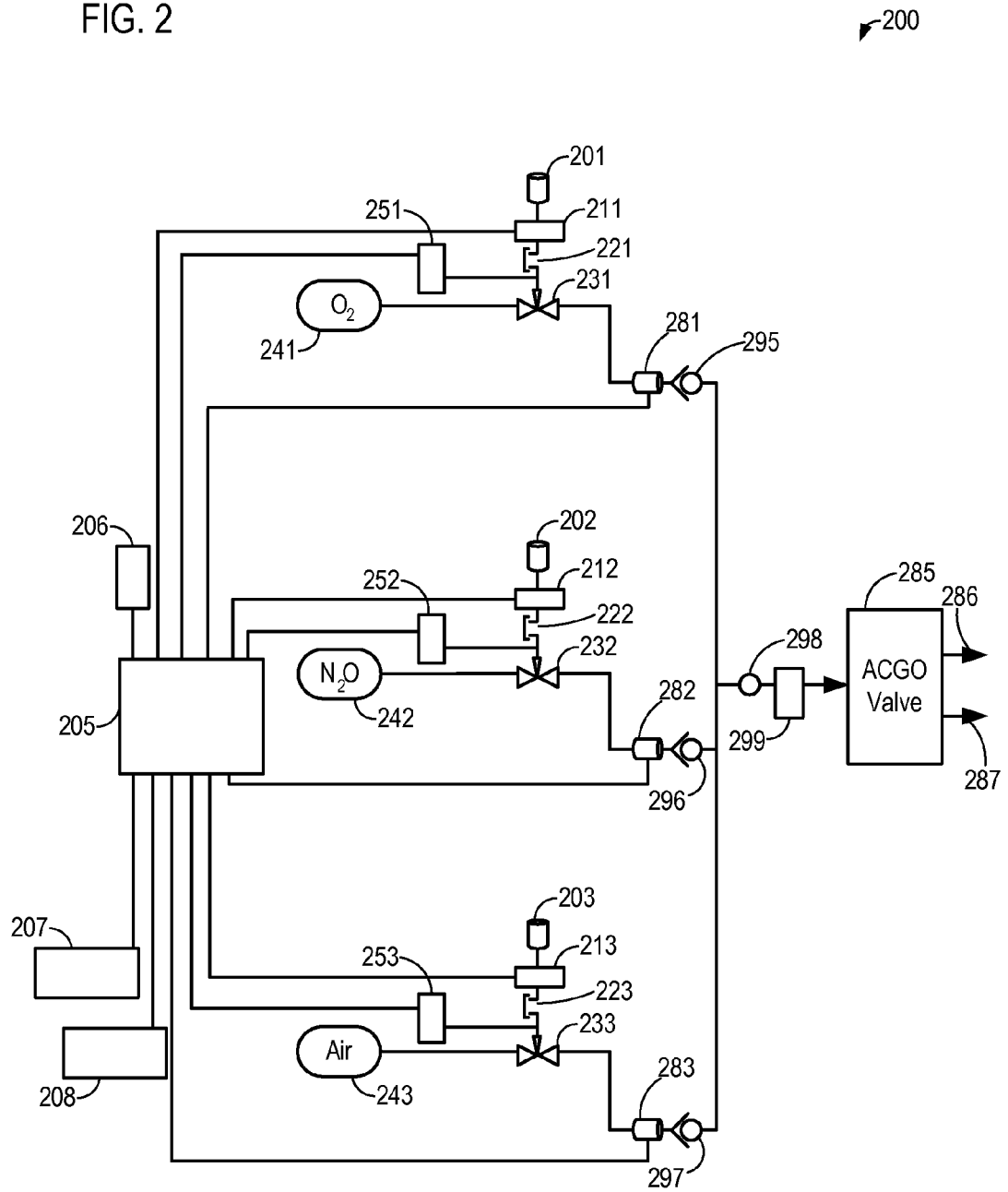
FIG. 2 illustrates an alternative embodiment of an anesthesia delivery system in which the electronic controls for each of oxygen, nitrous oxide, and air utilize a stepper motor in combination with a mechanically operated needle valve.

FIG. 2 illustrates an alternative embodiment of an anesthesia delivery system 200 in which the electronic controls for each of oxygen 241, nitrous oxide 242, and air 243 utilize stepper motors 251, 252, and 253 in combination with manually actuated needle valves 231, 232, and 233. First, second, and third manually rotatable knobs 201, 202, and 203 may be used to control the flow rate of oxygen 241, nitrous oxide 242, and air 243, respectively, whether the anesthesia delivery system 200 is in an electronic mode or a manual mode.

In an electronic mode, the anesthesia delivery system 200 may utilize a controller 205 to electronically control the flow rate of gases and/or liquids. The controller 205 may implement various functions associated with electronic control of the flow rates of one or more of the gases 241, 242, and 243, receiving inputs from a practitioner via various peripheral devices, and/or displaying information, such as telemetry data associated with a patient, to a practitioner and/or patient. For example, the anesthesia delivery system 200 may also utilize a touch pad 206 to receive inputs from a practitioner and/or a patient. The anesthesia delivery system 200 may also utilize a display 207 and/or a touch screen 208 when in an electronic mode. The electronic control of the flow rates of one or more gases may be implemented via hardware, firmware, and/or software distinct from other electronic controls, microprocessors, and/or the like.

In an electronic mode, a flow rate selection made via one or more of the manually rotatable knobs 201, 202, and 203 may be electronically encoded by an associated encoder 211, 212, and 213. The controller 205 may receive the electronically encoded selection(s) from the encoder(s) 211, 212, and 213. The controller 205 may then transmit a corresponding control signal to one or more of the stepper motors 251, 252, and 253, respectively. The stepper motors 251, 252, and 253 may adjust the needle valves 231, 232, and 233 to control the flow of each of the gases 241, 242, and 243.

For example, in an electronic mode, a manual adjustment of manually rotatable knob 201 by a practitioner may be encoded by the encoder 211. The controller 205 may then send a control signal to the stepper motor 251 in order to cause the stepper motor 251 to adjust the flow rate of oxygen 241 through the needle valve 231. The clutches 221, 222, and 223 may disengage the manually rotatable knobs 201, 202, and 203 from the needle valves 231, 232, and 233 to prevent manual adjustment of the needle valves 231, 232, and 233 when the gas flow rate system is in an electronic mode.

In a manual mode, or in the event of an electronic malfunction, the controller 205, the touchpad 206, the display 207, the touch screen 208, the encoders 211, 212, and 213, and/or the stepper motors 251, 252, and 253 may not function and/or may function incorrectly. According to various embodiments, the manually rotatable knobs 201, 202, and 203 may continue to allow for the uninterrupted control of the flow rate of the gases 241, 242, and 243. The clutches 221, 222, and 223 may engage the manually rotatable knobs 201, 202, and 203 with needle valves 231, 232, and 233, such that the manually rotatable knobs 201, 202, and 203 are operable to manually control the flow of the associated gases 241, 242, and 243 through the needle valves 231, 232, and 233.

In some embodiments, the clutches 221, 222, and 223 may disengage the stepper motors 251, 252, and 253 from the needle valves 231, 232, and 233. In some embodiments, a diversion valve or valve combination may direct a flow of a gas to different valves based on whether the system is in an electronic or manual mode.

Whether electronically controlled in an electronic mode or manually controlled in a manual mode, the flow rate of each gas 241, 242, and 243 may be measured by a flow rate measurement device 281, 282, and 283. The total flow rate may be displayed on the display 207 in an electronic mode or via a mechanical display in a manual mode. Check valves 295, 296, and 297 may prevent backflows of gases 241, 242, and 243. A total-flow measurement device 298 may measure the combined flow rate of the gases 241, 242, and 243. A vaporizer 299 may inject, or otherwise allow for the vaporization of, one or more anesthetics into the gases 241, 242, and 243.

As previously described, the output gas mixture, including one or more gases and/or anesthetics, may be directed to an ACGO valve 285. The ACGO valve 285 may be an electronically controlled valve switch, such as, for example, a drive gas controlled piloted shuttle valve. Electronic inputs and/or signals from the controller 205, the touchpad 206, the display 207, and/or the touch screen 208 may control the ACGO valve 285.

For example, an operator may utilize the touchpad 206, touch screen 208, and/or other electronic input to selectively divert the gas mixture either to the primary breathing system 286 or to the ACGO 287. The electronic signals may actuate and/or toggle a selector valve, such as a bi-stable latching selector valve, to cause a drive gas to toggle the position of a piloted shuttle valve. The piloted shuttle valve may direct the gas mixture to one of two outputs, depending on the position of an internal piston, as described herein.

Figure 3:
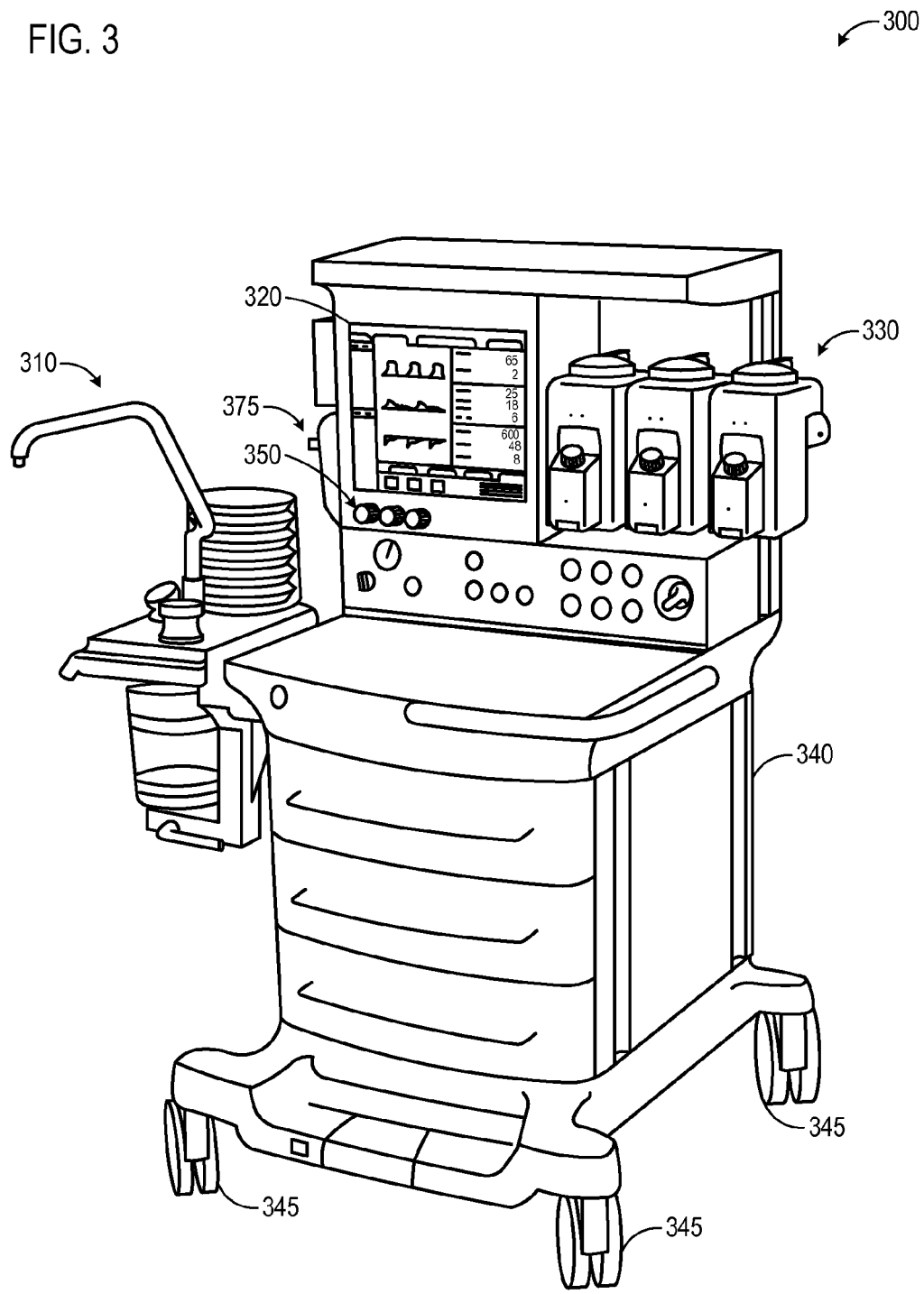
FIG. 3 illustrates an anesthesia delivery machine configured with three manual flow selectors, one each for controlling the flow of oxygen, nitrous oxide, and air.

FIG. 3 illustrates an anesthesia delivery machine 300 configured with three manual flow selectors 350, one each for controlling the flow of oxygen, nitrous oxide, and air. The anesthesia delivery machine 300 may include a primary breathing system 310, anesthetic gas vaporizers 330, and/or other components of an anesthetic delivery system. The anesthesia delivery machine 300 may include a cart 340 and/or wheels 345 for portability. An electronic display 320 may provide information regarding the flow rate and/or anesthetic delivery process to a practitioner. Additionally, the electronic display 320 may be configured as a touch-sensitive display to allow a practitioner to provide a selection of a flow rate electronically.

The anesthesia delivery machine 300 may include an ACGO 375 and an ACGO selector valve (not shown). In some embodiments, the ACGO selector valve may comprise an electronically controlled selector valve, such as an ACGO selector valve utilizing an electronically controlled drive gas for selectively toggling a piston within a piloted shuttle valve. In other embodiments, the ACGO selector valve may be a manually controlled and/or pneumatically controlled selector valve.

Figure 4:
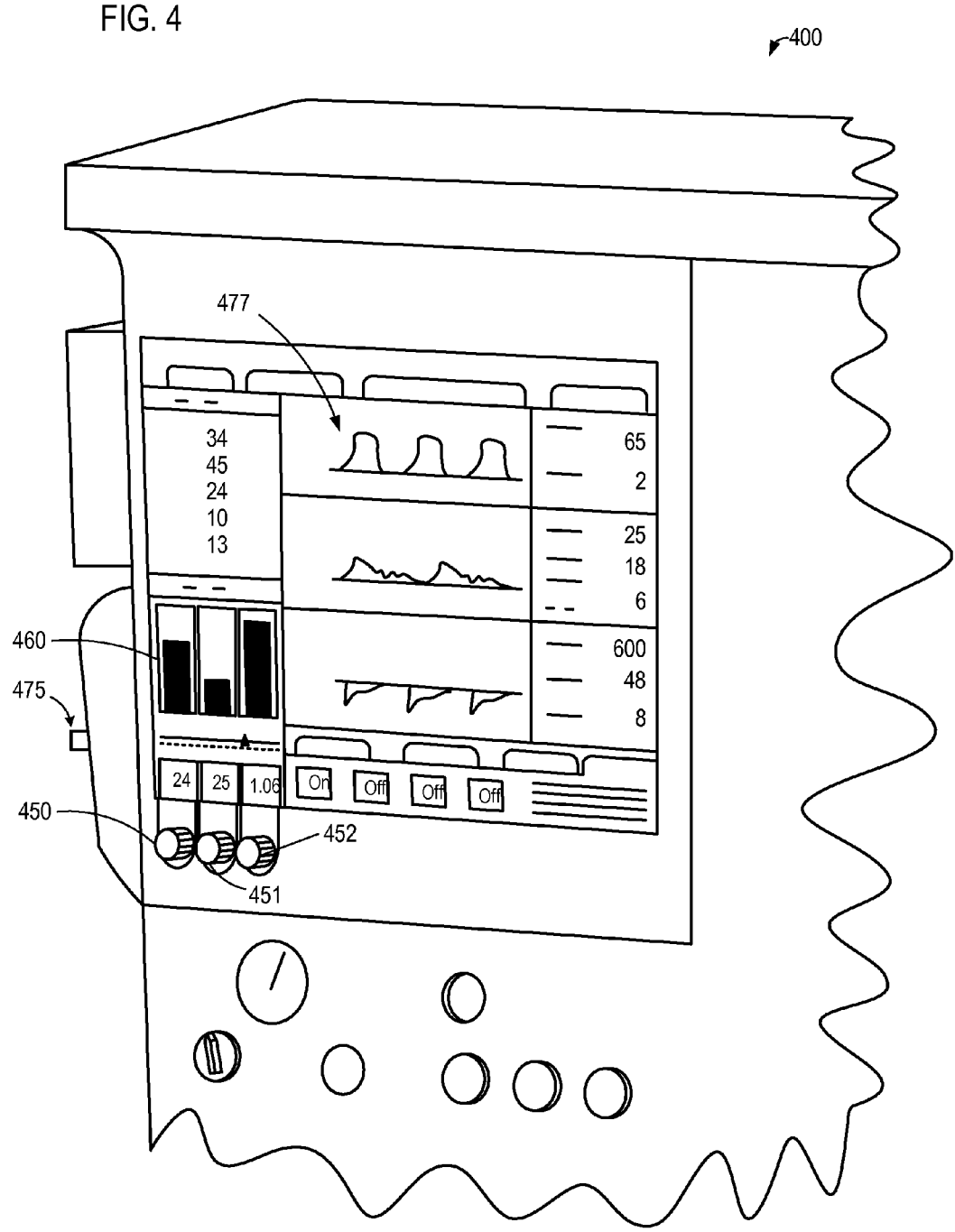
FIG. 4 illustrates a close-up view of electronic flow selector knobs configured to function as manual flow selector knobs in the event power is unavailable or lost.

FIG. 4 illustrates a close-up view 400 of electronic flow selector knobs 450, 451, and 452 configured to function as manual flow selector knobs in a manual mode. As illustrated, a display 477 may provide various telemetry data associated with a patient to a practitioner. The display 477 may also provide touch control of the anesthesia machine. The flow selector knob 450 may be used to control the flow of oxygen, the flow selector knob 451 may be used to control the flow of nitrous oxide, and the flow selector knob 452 may be used to control the flow of air. A practitioner may manually rotate each of the flow selector knobs 450, 451, and 452 in order to select a desired flow of one or more of the available gases.

Flow rate displays 460 may indicate a selected flow rate of each of the gases associated with each of the knobs 450, 451, and 452. In some embodiments, the flow rate displays 460 may be electronic. In other embodiments, the flow rate displays 460 may be mechanical, such that they are capable of displaying an associated flow rate even in a manual mode. In other embodiments, the flow rate displays 460 may be electronic or electronically enhanced when in an electronic mode and mechanical when in a manual mode.

While the illustrated embodiments show three flow selector knobs 450, 451, and 452, any number of flow selectors and associated gases may be utilized. For example, a flow control system may be configured to allow for the electronic and backup manual control of one, two, three, four . . . or N number of gases or liquids. In some embodiments, more than one knob may be configured to control the flow rate of the same gas.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient.

Although the flow rate of the various gases may be controlled via manual flow selector knobs 450, 451, and 452, the resulting gas mixture may be electronically directed either to a primary breathing system or to an ACGO 475. In some embodiments, an operator may utilize an electronic switch, button, slider, touch screen, touch pad, and/or other electronic input to selectively direct the gas mixture (including any anesthetics) to the ACGO 475 instead of the primary breathing system.

Figure 5:
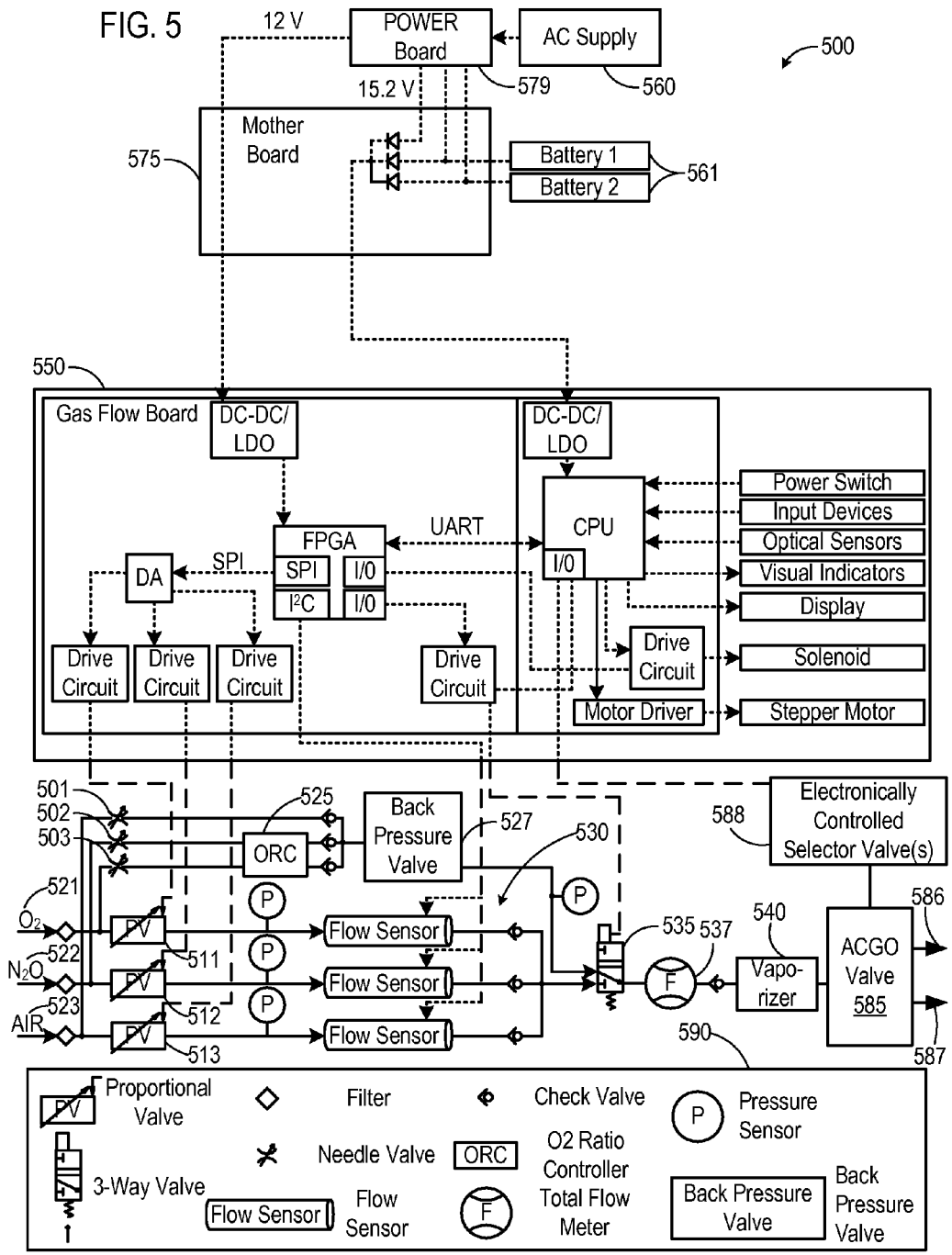
FIG. 5 illustrates a diagram of an anesthesia delivery system configured with electronic and backup manual controls for controlling the flow of oxygen, nitrous oxide, and air.

FIG. 5 illustrates a diagram 500 of an anesthesia delivery system configured with electronic flow control valves 511, 512, and 513 and backup manual flow control valves 501, 502, and 503 for controlling the flow of oxygen 521, nitrous oxide 522, and air 523. When power is available via AC supply 560 and/or batteries 561, the anesthesia delivery system may utilize electronic flow control valves 511, 512, and 513 controlled by one or more electronic flow selectors. The power input may be converted and/or inverted as necessary by a power board 579 and/or motherboard 575. A gas flow board 550 may include various monitoring and/or control components for electronically monitoring, regulating, and/or controlling the flow of gases within the anesthesia delivery system.

In various embodiments, the anesthesia delivery system may include various components and/or interface with various components via the gas flow board 550. For example, the gas flow board 550 may include and/or communicate with various FPGAs, CPUs, microprocessors, logic circuits, drive circuits, digital to analog converters, analog to digital converters, drive circuits, motor drivers, power switches, input devices, optical sensors, visual indicators, displays, solenoids, stepper motors, touch panels, and/or peripheral devices. Additionally, the gas flow board 550 may include and/or communicate with motor position switches, LEDs, needle valve switches, gas sources, and/or other selection inputs. A practitioner may interact with the anesthesia delivery system by providing inputs with regard to a flow of one or more gases. For instance, a practitioner may provide an input via an electronic flow selector. The electronic flow selector may comprise a mechanically rotatable knob and a rotary encoder.

When the anesthesia delivery system is in a powered state, the user may utilize an electronic mode or select a manual mode. When the anesthesia delivery system is in an unpowered state, the anesthesia delivery system may be used in a manual mode. In the electronic mode, the three source gases, oxygen 521, nitrous oxide 522, and air 523, may flow through the electronic flow control valves 511, 512, and 513, an oxygen ratio controller 525, and/or check valves 530 and flow sensors. In a manual mode, the three source gases 521, 522, and 523 may flow through backup manual flow control valves 501, 502, and 503, oxygen ratio controller 525, and/or back pressure valve 527.

In various embodiments, a user may achieve a desired ratio of gases 521, 522, and 523 by starting with zero flow and sequentially adding source gases to the total flow, noting the effect of each on total flow rate. In an alternative embodiment, the user may achieve a desired ratio of gases 521, 522, and 523 by starting at a "home state" flow of oxygen 521 and then adjusting each of the gases 521, 522, and 523 to achieve the desired flow rate. The oxygen ratio controller 525 may ensure a clinically safe ratio of oxygen to nitrous oxide. The check valves 530 may prevent back flow of gases 521, 522, and 523 due to potentially higher downstream pressures.

According to various embodiments, a user may select a flow rate of a combination of oxygen and air to be supplied to a patient. A user may also select a flow rate of nitrous oxide to be provided to a patient instead of air. In some embodiments, the nitrous oxide may be supplied in addition to air. Regardless of the selections made by a user, an oxygen ratio controller (ORC) 525 may ensure that a safe amount of oxygen is supplied to the patient.

In either flow control mode, after passing through the check valves 530, the flows of the three gases 521, 522, and 523 may be combined into a single flow as a gas mixture, which may be measured by a total flow meter 537. An anesthetic gas vaporizer 540 may vaporize an anesthetic into the gas mixture. A three-way selector valve 535 may be used to direct a flow of gases from only one of the backup manual flow control valves 501, 502, and 503 and the electronic flow control valves 511, 512, and 513. Alternatively, the three-way selector valve 535 may comprise one or more normally-open and/or normally-closed valves. Alternative diversion valve systems may be employed in place of a three-way selector valve 535 and/or normally-open and/or normally-closed valves.

The gas mixture, and any vaporized anesthetics, may then be directed by an ACGO valve 585 either to a primary breathing system 586 or to an ACGO 587. The ACGO valve 585 may include a piloted shuttle valve configured to switch the flow of the gas mixture based on a drive gas controlled by one or more electronically controlled selector valves 588. The electronically controlled selector valves 588 may be controlled by an electronic signal from a CPU or another electronic signal or drive circuit of gas flow board 550.

In some embodiments, the ACGO valve 585 may include a shuttle valve, such as a piloted shuttle valve actuated by drive gases. The piloted shuttle valve may selectively direct the flow of a gas mixture between the primary breathing system 586 and the ACGO 587 based on an input drive gas from the electronically controlled selector valves 588. In some embodiments, the piloted shuttle valve may direct a gas mixture to the primary breathing system 586 in a default state due to a bias from a resilient member, such as a spring or tensioned plate. By directing a drive gas into the piloted shuttle valve, via the selector valves 588, the gas mixture can be switched to flow to the ACGO 587.

The piloted shuttle valve may include a valve body and a piston configured to translate within the valve body. The valve body may include an inlet for a gas mixture and two outlets for the gas mixture. The piston may divert the gas mixture to a primary breathing system outlet when translated to a first position and to an ACGO when translated to a second position. In some embodiments, the valve body may include a second drive gas inlet. The piston may be translated between the first and second positions by selectively driving gas in the first and second drive gas inlets. Alternatively, the valve body may include a single drive gas inlet, and the piston may be biased or default to one of the two positions. For example, the valve body may include a resilient member, such as a spring, on one end of the piston to cause the piston to default to the first position. The drive gas may be configured to allow a drive gas to selectively drive the piston to the second position, against the resilient member. In another embodiment, the drive gas may be selectively directed to either end of the piston based on a network of shuttle valves controlled by a three-way selector valve. The three-way selector valve may be a latching, bi-stable selector valve.

The piloted shuttle valve may also include one or more pressure relief valves and/or position detection switches. The piloted shuttle valve may also include guards and/or covers for any of the various components, such as a switch guard to protect a position detection switch.

In an electronic mode, flow control selectors associated with the backup manual flow control valves 501, 502, and 503 may be disabled, retracted, locked, and/or otherwise disengaged. In a manual mode (whether entered due to power loss or user selection), flow control selectors associated with the manual flow control valves 501, 502, and 503 may be enabled, deployed, unlocked, and/or otherwise engaged. Various elements of the diagram 500 are illustrated in the key 590 and are not described in detail herein. Additionally, any of a wide variety of components, measurement devices, monitoring devices, and/or control devices configured for use in anesthesia delivery systems, gas delivery systems, liquid delivery systems, and/or other related systems may be added to, supplemented within, and/or replace components within the illustrated system.

Figure 6:
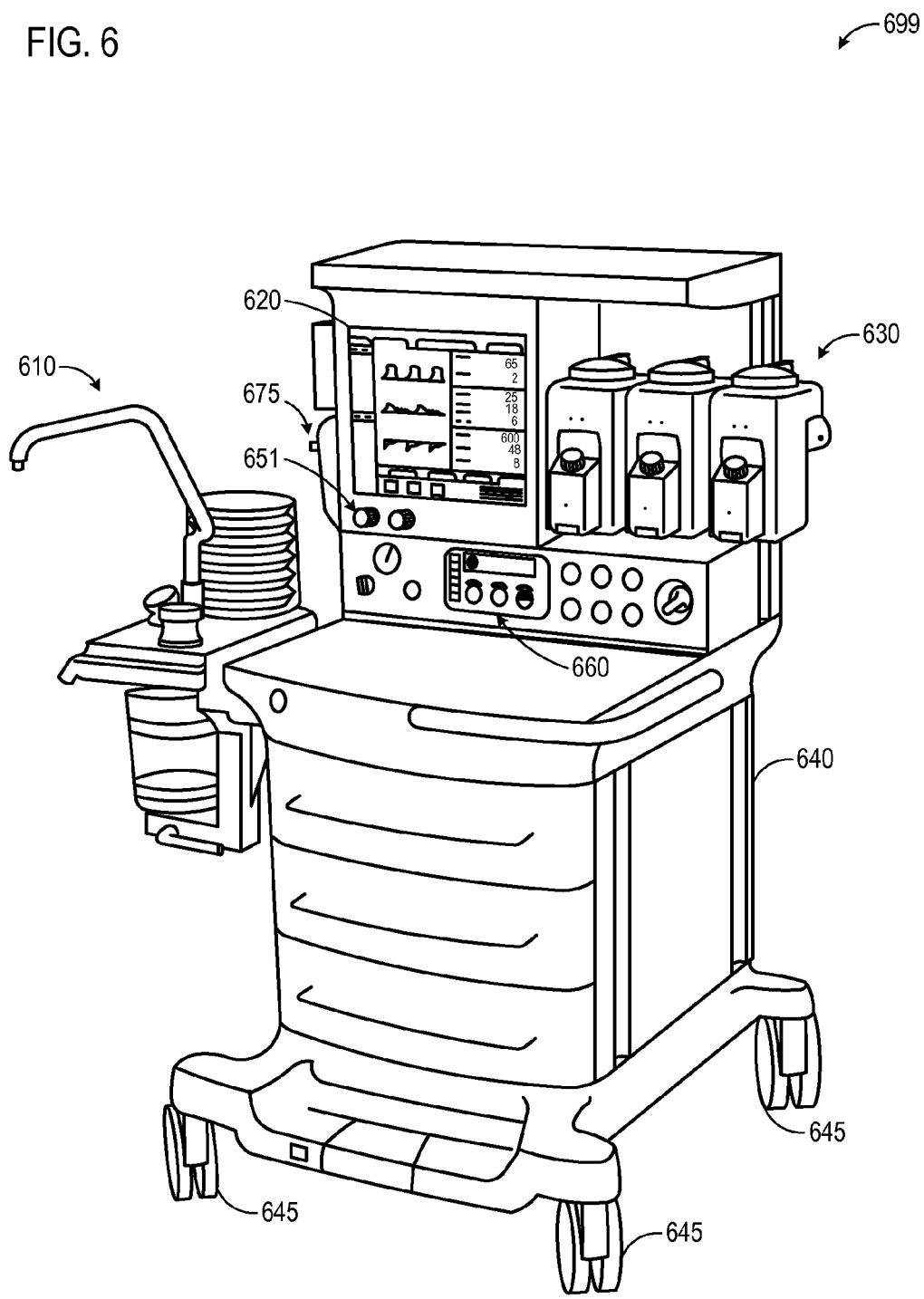
FIG. 6 illustrates an anesthesia delivery machine configured with two electronic flow control selectors, configurable to selectively control each of the three gases, and three backup manual flow selectors for controlling each of the three gases.

FIG. 6 illustrates an anesthesia delivery machine 699 configured with two electronic flow control selectors 651, configurable to selectively control each of the three gases, and three backup manual flow selectors 660 for controlling each of the three gases. The anesthesia delivery machine 699 may include a primary breathing system 610, anesthetic gas vaporizers 630, and/or other components of an anesthetic delivery system. The anesthesia delivery machine 699 may include a cart 640 and/or wheels 645 for portability. An electronic display 620 may provide information regarding the flow rate and/or anesthetic delivery process to a practitioner. Additionally, the electronic display 620 may be configured as a touch-sensitive display to allow a practitioner to provide a selection of a flow rate.

The three backup manual flow selectors 660 may remain retracted and/or disabled when the anesthesia delivery machine 699 is in an electronic mode. When the anesthesia delivery machine 699 enters a manual mode (e.g., due to power loss or a user selection), the three backup manual flow selectors 660 may be deployed, unlocked, and/or otherwise function. As previously described, various internals, switches, normally-open valves, normally-closed valves, three-way valves, and/or other components may regulate the flow of gases within the anesthesia delivery machine 699 based on whether it is in a manual mode or an electronic mode.

The anesthesia delivery machine 699 may include an ACGO 675. The gas mixture selected via electronic flow control selectors 651 or backup manual flow selectors 660 may be directed to the primary breathing machine 610 or the ACGO 675. An electronically controlled ACGO valve may allow a user to electronically select whether the gas mixture is directed toward the primary breathing machine 610 or the ACGO 675. As in previous embodiments, the ACGO selector may utilize an electronically controlled drive gas for selectively toggling a piston within a piloted shuttle valve.

Figure 7:
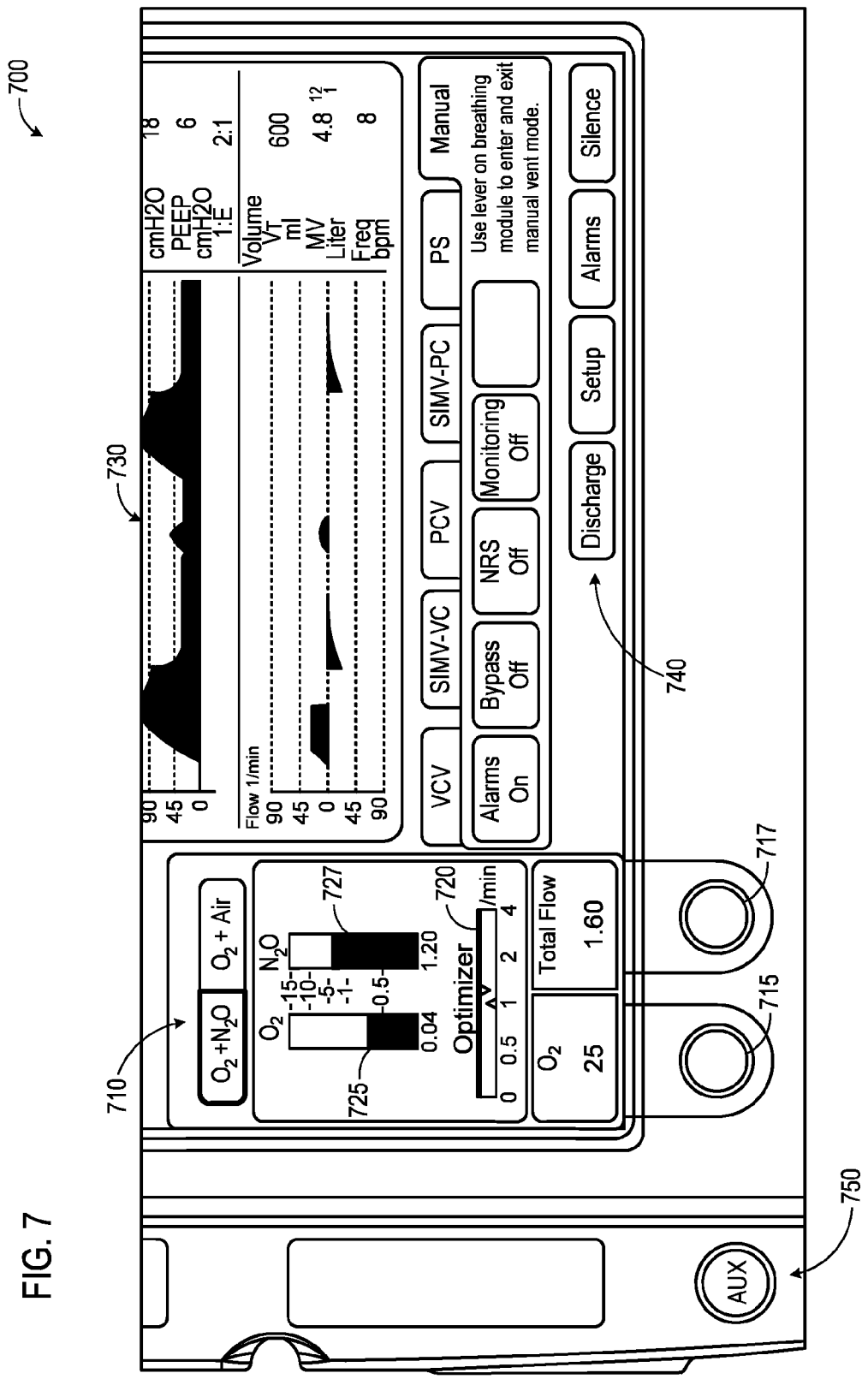
FIG. 7 illustrates a close-up view of a control panel of an anesthesia delivery machine, including two electronic flow control selectors selectively configurable to control either oxygen and nitrous oxide, or oxygen and air.

FIG. 7 illustrates a close-up view of a control panel 700 of an anesthesia delivery machine, including two electronic flow control selectors 715 and 717 selectively configurable to control either oxygen and nitrous oxide, or oxygen and air. As illustrated, the anesthesia delivery machine may include a panel 730 to display various telemetry data associated with a patient, information associated with the flow rate of gases, and/or information associated with the delivery of one or more anesthetics. Various inputs 740 may be available to change the display of panel 730 and/or to control the anesthesia delivery machine.

In a first position, a selection toggle 710 may allow a practitioner to control the flow rate of oxygen and nitrous oxide via the respective electronic flow control selectors 715 and 717. In a second position, the selection toggle 710 may allow a practitioner to control the flow rate of oxygen and air via the respective flow control selectors 715 and 717. Depending on the position of the selection toggle 710, various flow rate monitoring devices and ratio measuring devices 720, 725, and 727 may indicate the flow rate of one or more gases and/or combination of gases.

While the illustrated embodiment shows two electronic flow control selectors 715 and 717, any number of flow control selectors and associated gases may be utilized. For example, a flow control system may be configured to allow for the electronic and backup manual control of one, two, three, four . . . or N number of gases or liquids. In some embodiments, more than one flow control selector (e.g., knob, toggle, dial, slider, switch) may be configured to control the flow rate of the same gas. Additional selection toggles 710 and/or a multi-position selection toggle may be used to control the number of gases controlled by any number of corresponding flow control selection knobs. The flow control selectors may include and/or utilize any analog or digital selection mechanism for selecting a flow rate, including knobs as illustrated in the figures.

In various embodiments, an ACGO may be selected via an electronic button 750. Additionally and/or alternatively, the ACGO may be selected via the various inputs 740 and/or the display of panel 730. The ACGO electronic button 750 may actuate one or more selector valves to control drive gases, causing the drive gases to actuate a piloted shuttle valve. The piloted shuttle valve may selectively direct the gas mixture to the ACGO instead of the primary breathing machine.

Figure 8:
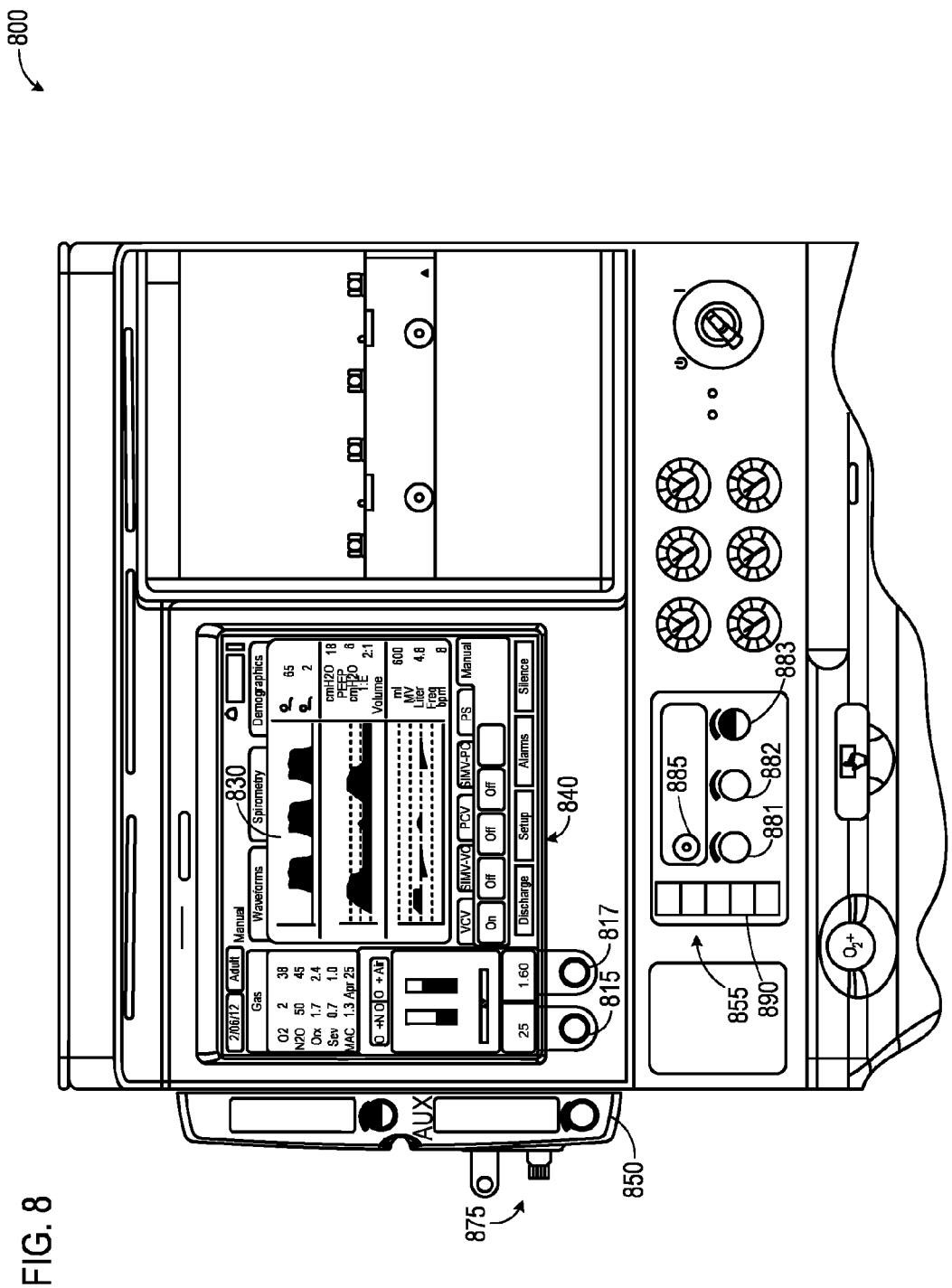
FIG. 8 illustrates a wider view of a control panel of an anesthesia delivery machine, including backup manual flow controls for controlling the flow of three gases independently.

FIG. 8 illustrates a wider view of a control panel 800 of an anesthesia delivery machine, including an ACGO 875 and an electronic control 850 for selecting the ACGO 875 instead of the primary breathing machine. The anesthesia delivery machine may also include a manually actuated control for selecting the ACGO 875. A gas mixture selected by the various controls described below may be directed to either the ACGO 875 or the primary breathing machine via a piloted shuttle valve. The piloted shuttle valve may be pneumatically actuated by a drive gas controlled by an electronic selector valve.

The anesthesia delivery machine may include backup manual flow control selectors 881, 882, and 883 for controlling the flow of three gases independently. When the anesthesia delivery system is in a powered state and the user has not selected a manual mode, the anesthesia delivery system may be in an electronic mode. In an electronic mode, two electronic flow control selectors 815 and 817 may be used to control either oxygen and nitrous oxide or oxygen and air, depending on the selection made via a selection toggle. An electronic display 830 may display information associated with the flow rate of one or more gases, an anesthetic, and/or patient telemetry data. Various touch inputs 840 may be available.

When the anesthesia delivery system is in an unpowered state and/or the user has selected a manual mode, the anesthesia delivery system may be in a manual mode. In a manual mode, the flow rate of one or more gases and/or the amount of anesthetic delivery may be controlled via a manual panel 855. The electronic display 830, the touch inputs 840, the electronic flow control selectors 815 and 817, and other electronic components may be unavailable in an unpowered state, and one or more of them may be unavailable and/or otherwise disabled in a manual mode selected when in a powered state.

The manual panel 855 may include a total flow rate indicator 890, a manual mode selector 885 (e.g., a spring-loaded plunger), and one or more manually operated flow control selectors 881, 882, and 883. According to various embodiments, a manually operated flow control selector may be available for each available gas or for each available critical gas. In various embodiments, manually operated flow control selectors 881, 882, and 883 may be disabled, retracted, locked, and/or otherwise not operational when the anesthesia delivery system is in an electronic mode. In a manual mode, the manually operated flow control selectors 881, 882, and 883 may be enabled, deployed, unlocked, and/or otherwise become operational.

Figure 9:
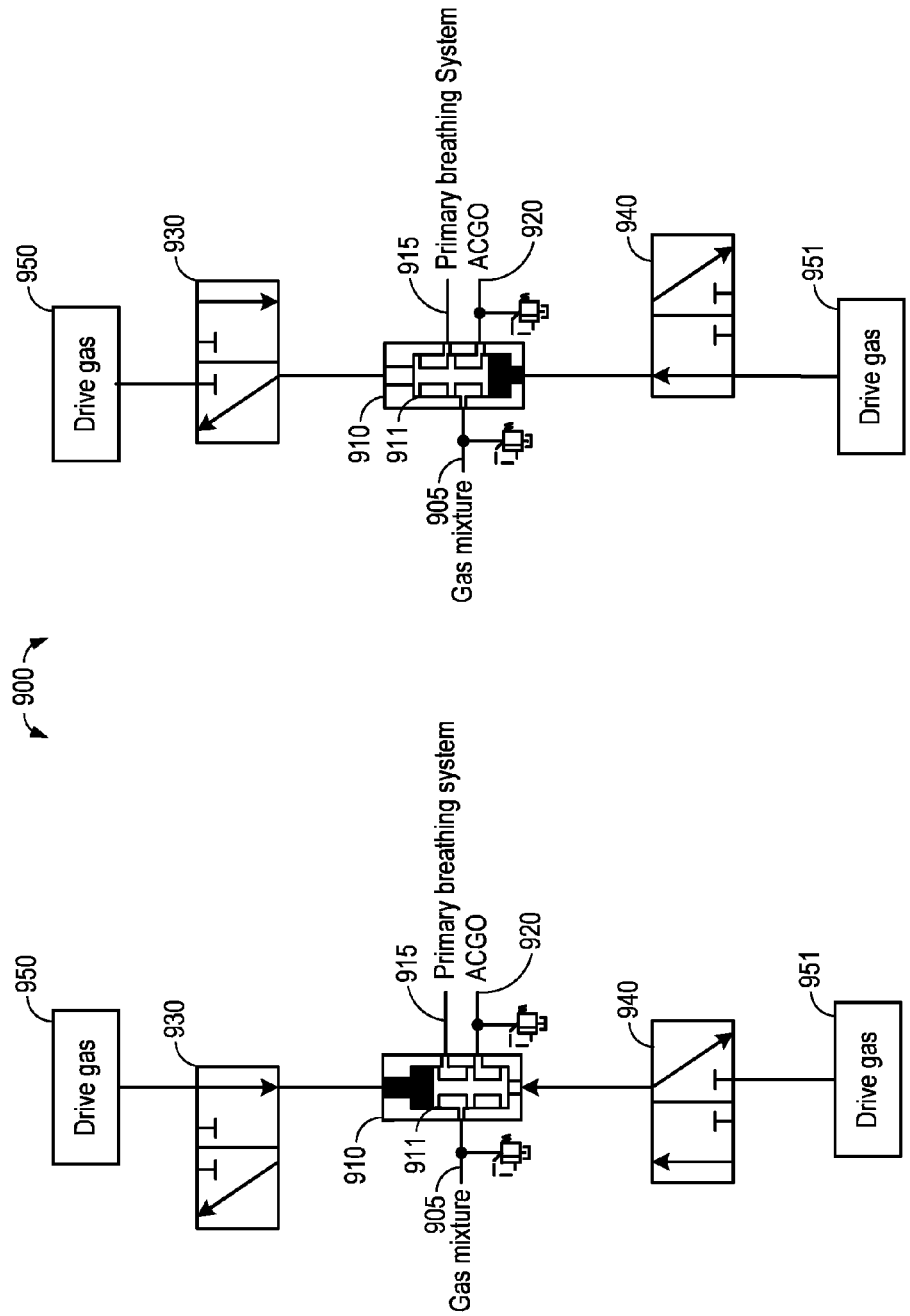
FIG. 9A illustrates a diagram of a valve system, including a piloted shuttle valve driven to a first state by a first drive gas such that a gas mixture is directed to a primary breathing system.
FIG. 9B illustrates a diagram of the valve system of FIG. 9A, with the piloted shuttle valve driven to a second state by a second drive gas, such that a gas mixture is directed to an auxiliary common gas output.

FIG. 9A illustrates a diagram of an ACGO valve system 900, including a piloted shuttle valve 910 driven to a first state by a first drive gas 950 such that a gas mixture 905 is directed to a primary breathing system 915. As illustrated, the piloted shuttle valve 910 may include an internal piston 911 configured to translate between a first position (shown in FIG. 9A) and a second position (shown in FIG. 9B). To divert the gas mixture 905 to the primary breathing system 915, an electronically controlled latching selector valve 930 may cause the first drive gas 950 to flow to a first drive gas inlet on the piloted shuttle valve 910. An electronically controlled latching selector valve 940 may prevent a second drive gas 951 from flowing to a second drive gas inlet on the piloted shuttle valve 910. Accordingly, the drive gas 950 may cause the piston 911 to translate to a first position, in which the gas mixture 905 flows through a piston channel to the primary breathing system 915. In various embodiments, the first drive gas 950 and the second drive gas 951 may be the same drive gas from the same source, the flow of which is controlled by the first and second latching selector valves 930 and 940.

FIG. 9B illustrates a diagram of the ACGO valve system 900, with the piloted shuttle valve 910 driven to a second state by the second drive gas 951, such that the gas mixture 905 is directed to the ACGO 920. To divert the gas mixture 905 to the ACGO 920, the electronically controlled latching selector valve 930 may prevent the drive gas 950 from flowing to the first drive gas inlet on the piloted shuttle valve 910. The electronically controlled latching selector valve 940 may allow the second drive gas 951 to flow to the second drive gas inlet on the piloted shuttle valve 910. The second drive gas 951 may cause the piston 911 to translate to a second position, in which the gas mixture 905 flows through a second piston channel to the ACGO 920.

As illustrated, the first piston channel may be connected to the primary breathing system, and the second piston channel may be connected to the ACGO. By translating the piston 911 between a first and second position, the gas mixture 905 input may be toggled between the first and second piston channels. The piston 911 may prevent the first and second channels from connecting. Accordingly, the primary breathing system and the ACGO may remain independent from one another.

Comparing FIGS. 9A and 9B, it can be seen that by selectively toggling the latching selector valves 930 and 940, the gas mixture 905 can be diverted to either the primary breathing system 915 or the ACGO 920. The latching selector valves 930 and 940 may be controlled by an electronic interface and/or a backup manual interface. The illustrated configuration allows an ACGO valve to be electronically controlled via selector valves while the piloted shuttle valve 910 accommodates relatively high flow rates of the gas mixture and/or anesthetics, provides biocompatibility, operates in an oxygen-rich environment, and/or conveys potentially corrosive anesthetic agents.

Referring to both FIGS. 9A and 9B, the drive gas(es) 950 and 951 may be a pressurized gas, such as oxygen or air. Each of the latching selector valves 930 and 940 may be an electronically controlled pneumatic valve configured to remain stable in either an open or closed state. An electronic signal may cause each of the latching selector valves 930 and 940 to toggle states. The latching selector valves 930 and 940 may be configured such that only one is open at any given time.

Figure 10:
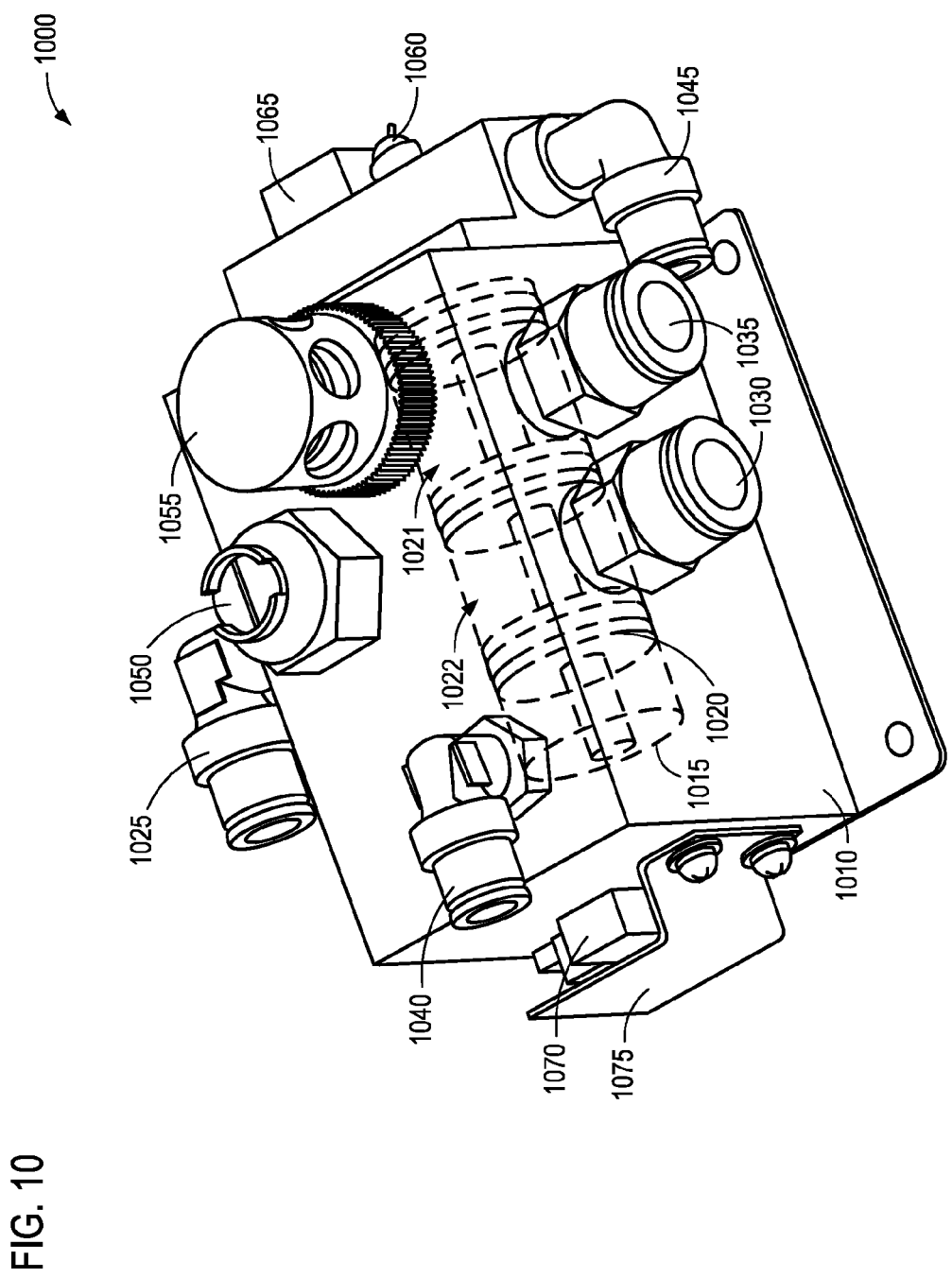
FIG. 10 illustrates a piloted shuttle valve configured to selectively direct a gas mixture to either a primary breathing system or an ACGO.

FIG. 10 illustrates a piloted shuttle valve 1000 configured to selectively direct a gas mixture to either a primary breathing system or an ACGO. The piloted shuttle valve may include a valve body 1010 configured with a piston chamber 1015. The piston chamber 1015 may be fluidly connected to a gas mixture inlet 1025, an ACGO 1035, and a primary breathing system outlet 1030. A piston 1020 may be configured to translate within the piston chamber 1015. The piston 1020 may include a first valve channel 1022 fluidly connected to the primary breathing system outlet 1030 and a second valve channel 1021 fluidly connected to the ACGO 1035.

In a first position, and as illustrated, the first valve channel 1022 may be fluidly connected to the gas mixture inlet 1025. In a second position, the second valve channel 1021 may be fluidly connected to the gas mixture inlet 1025. Accordingly, by translating the piston 1020 within the piston chamber 1015, the gas mixture is selectively directed through one of the first 1022 and second 1021 valve channels to either the primary breathing system outlet 1030 or the ACGO 1035, respectively.

The piston 1020 may be translated within the piston chamber 1015 based on pressure from a drive gas. One side of the piston chamber 1015 may be fluidly connected to a first drive gas inlet 1040, and the other side of the piston chamber 1015 may be fluidly connected to a second drive gas inlet 1045. A drive gas may be directed through one of the two drive gas inlets 1040 and 1045 in order to selectively translate the piston 1020 between the two sides of the piston chamber 1015. Accordingly, depending on which of the first and second drive gas inlets 1040 and 1045 is pressurized, a gas mixture may flow from the gas mixture inlet 1025 to either the primary breathing system outlet 1030 or the ACGO 1035.

The piston 1020 may include a piston stem 1060 on one or both ends (only one is visible). The piston stems 1060 may be configured to actuate either a position detection switch 1065 or a position detection switch 1070, depending on the location of the piston 1020 within the piston chamber 1015. A guard 1075 may be configured to provide physical protection for position detection switch 1070.

One or more of the valve channels 1021 and 1022, the piston chamber 1015, the inlets 1025, 1040, and 1045, and/or the outlets 1030 and 1035 may include pressure relief valves. For example, the gas mixture inlet 1025 may be fluidly connected to a pressure relief valve 1050 configured to maintain the pressure within the gas mixture inlet 1025 under approximately 37.9 kPa. As another example, the ACGO 1035 may be connected to a pressure relief valve 1055 configured to maintain the pressure below 11 kPa. The pressure within any component may, of course, be regulated to another pressure by using an alternative pressure relief valve.

Figure 11A:
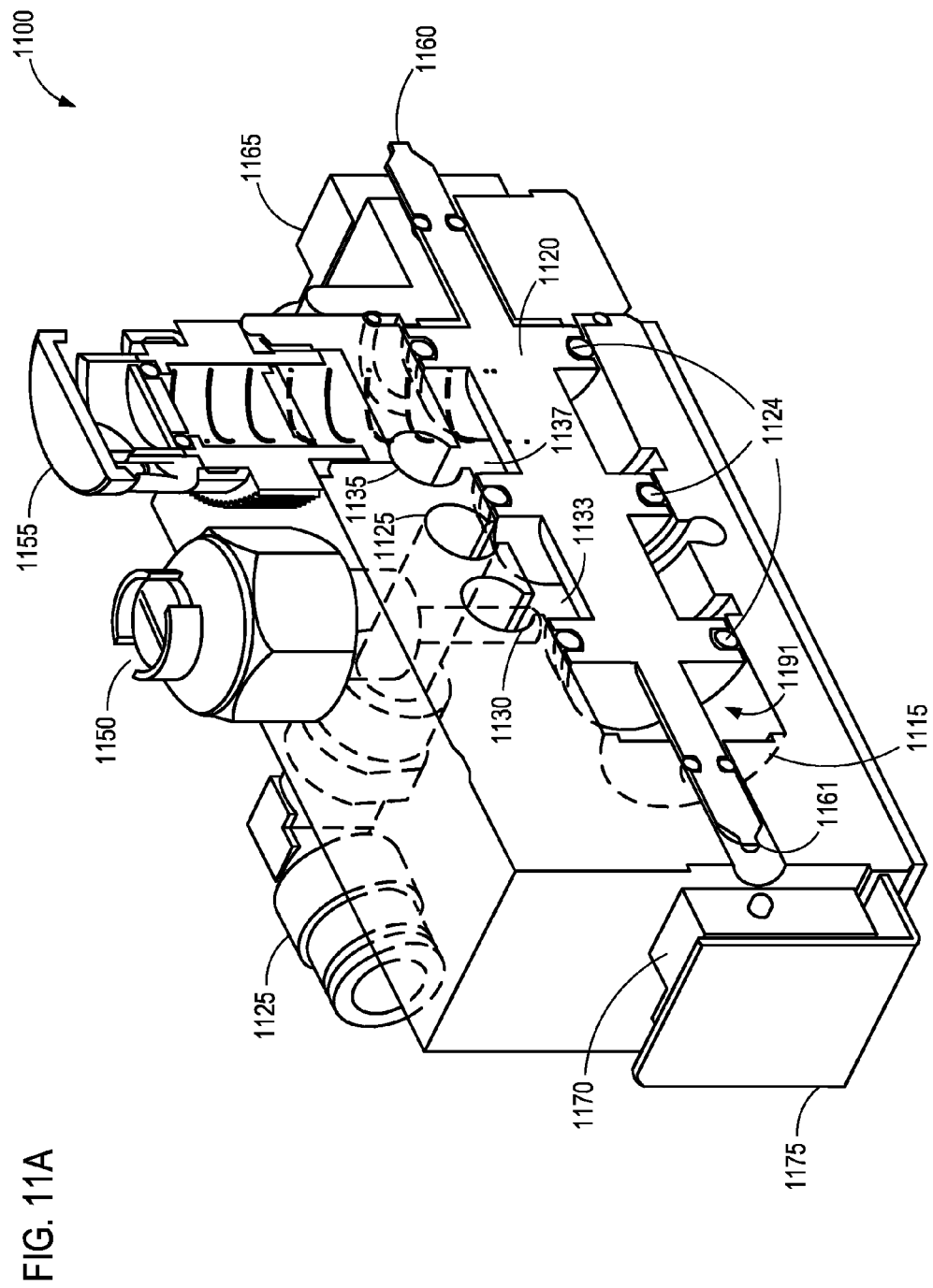
FIG. 11A illustrates a cross-sectional view of a piloted shuttle valve, including a gas mixture inlet, a primary breathing system outlet, an ACGO, and a translatable piston in a first position.

FIG. 11A illustrates a cross-sectional view of a piloted shuttle valve 1100, including a gas mixture inlet 1125, a primary breathing system outlet 1130, an ACGO 1135, and a translatable piston 1120 in a first position within a piston chamber 1115. The piston chamber 1115 may be fluidly connected to the gas mixture inlet 1125, the ACGO 1135, and the primary breathing system outlet 1130. The piston 1120 may include a first valve channel 1133 that is fluidly connected to the primary breathing system outlet 1130, and a second valve channel 1137 that is fluidly connected to the ACGO 1135.

In a first position, and as illustrated, the first valve channel 1133 may fluidly connect the gas mixture inlet 1125 to the primary breathing system outlet 1130. In a second position, the second valve channel 1137 may fluidly connect the gas mixture inlet 1125 to the ACGO 1135. Accordingly, by translating the piston 1120 within the piston chamber 1115, the gas mixture is selectively directed to either the primary breathing system outlet 1130 or the ACGO 1135.

The piston 1120 may include seals 1124 configured to fluidly separate the primary breathing system outlet 1130 from the ACGO 1135, and the outlets 1130 and 1135 from the drive gases (not pictured). A drive gas may exert a force on either end of the piston 1120 to translate the piston 1120 from a first position (illustrated in FIG. 11A) to a second position (illustrated in FIG. 11B). Specifically, a drive gas pressurized in a gap 1191 may cause the piston 1120 to translate to the first position illustrated in FIG. 11A. Similarly, a drive gas pressurized into a gap 1192 (FIG. 11B) may cause the piston 1120 to translate to the second position illustrated in FIG. 11B.

The piston 1120 may include a piston stem 1160 and 1161 on one or both ends. The piston stems 1160 and 1161 may actuate either a position detection switch 1165 or a position detection switch 1170, respectfully, depending on the location of the piston 1120 within the piston chamber 1115. A guard 1175 may be configured to provide physical protection for position detection switch 1170. Pressure relief valves 1150 and 1155 may be configured to limit the pressure within various areas of the system.

Figure 11B:
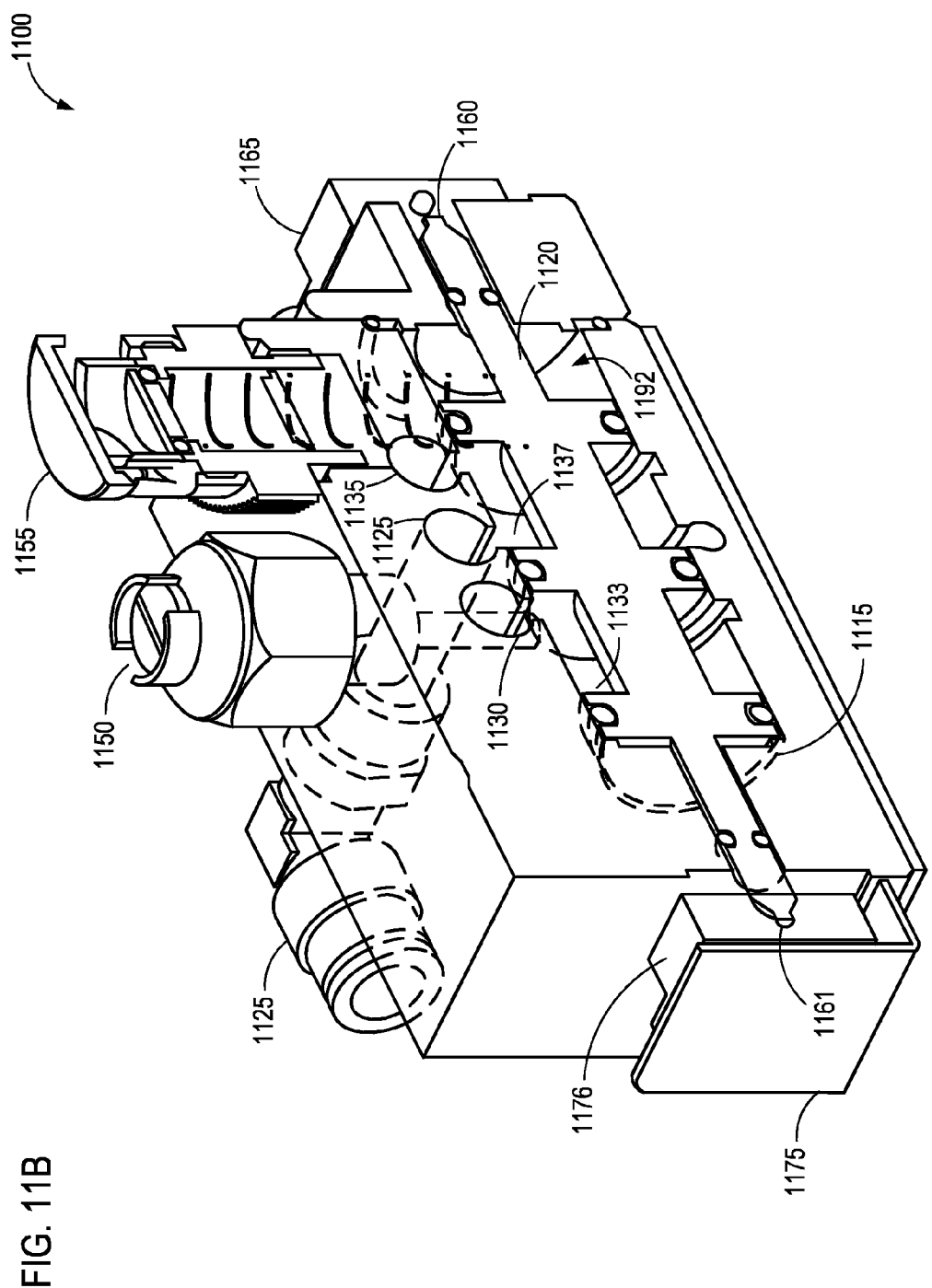
FIG. 11B illustrates a cross-sectional view of the piloted shuttle valve of FIG. 11A with the translatable piston in a second position.

FIG. 11B illustrates a cross-sectional view of the piloted shuttle valve 1100 with the piston 1120 in a second position within the piston chamber 1115. In the illustrated second position, the second valve channel 1137 may fluidly connect the gas mixture inlet 1125 to the ACGO 1135. Comparing FIGS. 11A and 11B, by translating the piston 1120 within the piston chamber 1115, the gas mixture is selectively directed to either the primary breathing system outlet 1130 (FIG. 11A) or the ACGO 1135 (FIG. 11B).

Figure 12:
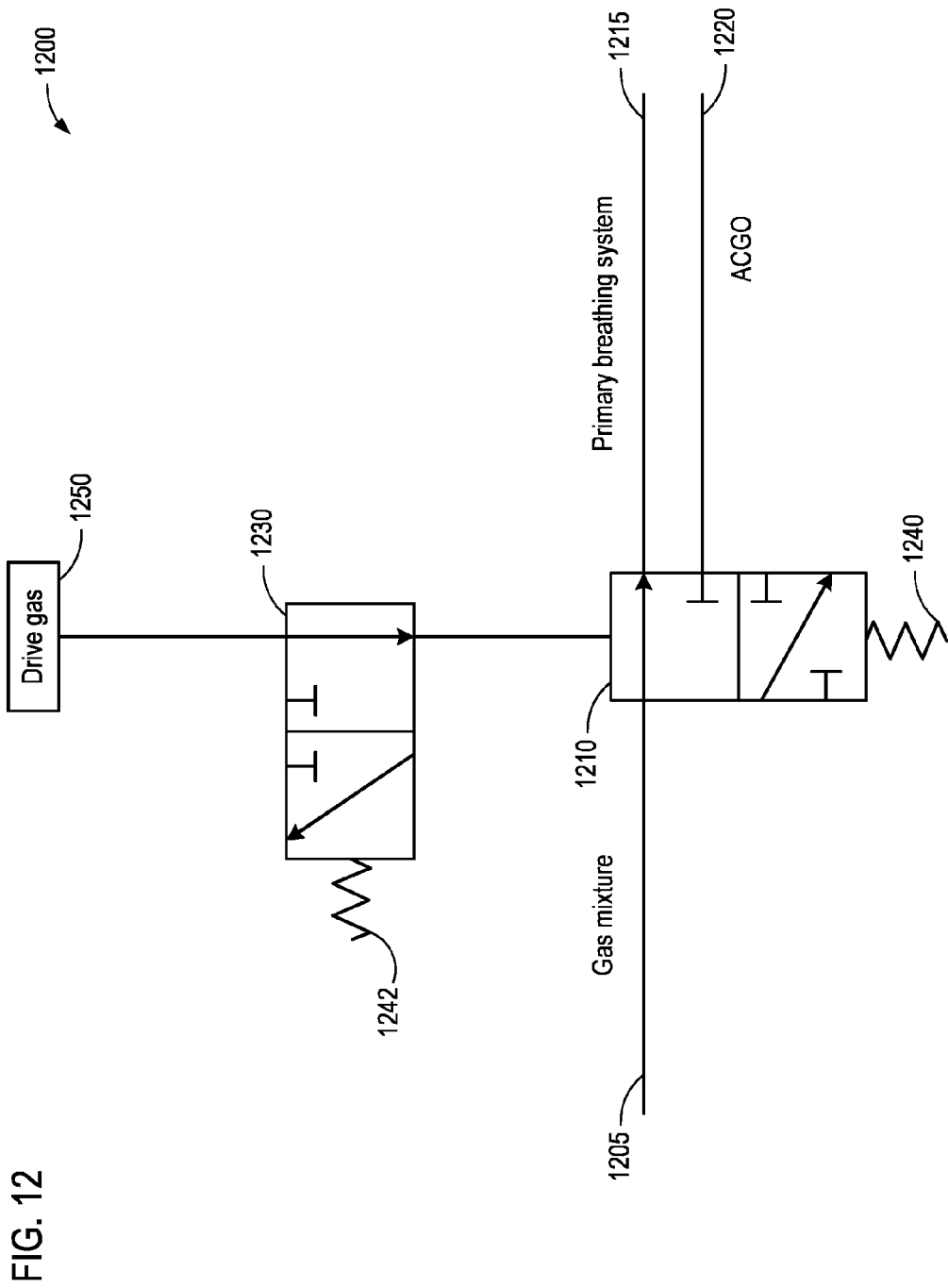
FIG. 12 illustrates a diagram of a valve system, including a spring-loaded shuttle valve, configured to selectively direct a gas mixture between a primary breathing system and an ACGO based on a single drive gas.

FIG. 12 illustrates a diagram 1200 of a valve system, including a spring-loaded shuttle valve 1210. A spring 1240 may be configured to bias the shuttle valve 1210, such that in a default position the shuttle valve 1210 may allow a gas mixture 1205 to flow to a primary breathing system 1215. An electronically controlled selector valve 1230 may selectively allow a pressurized drive gas 1250 to flow into the shuttle valve 1210. In a first state, the selector valve 1230 may prevent the drive gas 1250 from flowing to the shuttle valve 1210. Accordingly, an internal translatable piston within the shuttle valve 1210 may allow the gas mixture 1205 to flow through a first valve channel to the primary breathing system 1215.

In a second state, the selector valve 1230 may allow the drive gas 1250 to flow into a pilot inlet in the shuttle valve 1210. The pressure of the drive gas 1250 may cause the internal translatable piston within the shuttle valve 1210 to translate against and compress the spring 1240. The drive gas 1250 may translate the internal translatable piston to a second position in which the gas mixture 1205 flows through a second valve channel to an ACGO 1220. Accordingly, the gas mixture 1205 may be selectively diverted to either the primary breathing system 1215 or the ACGO 1220, depending on an electronic signal controlling the selector valve 1230. The selector valve 1230 may include a return spring 1242 to allow the drive gas to be evacuated from the shuttle valve 1210.

Figure 13B:
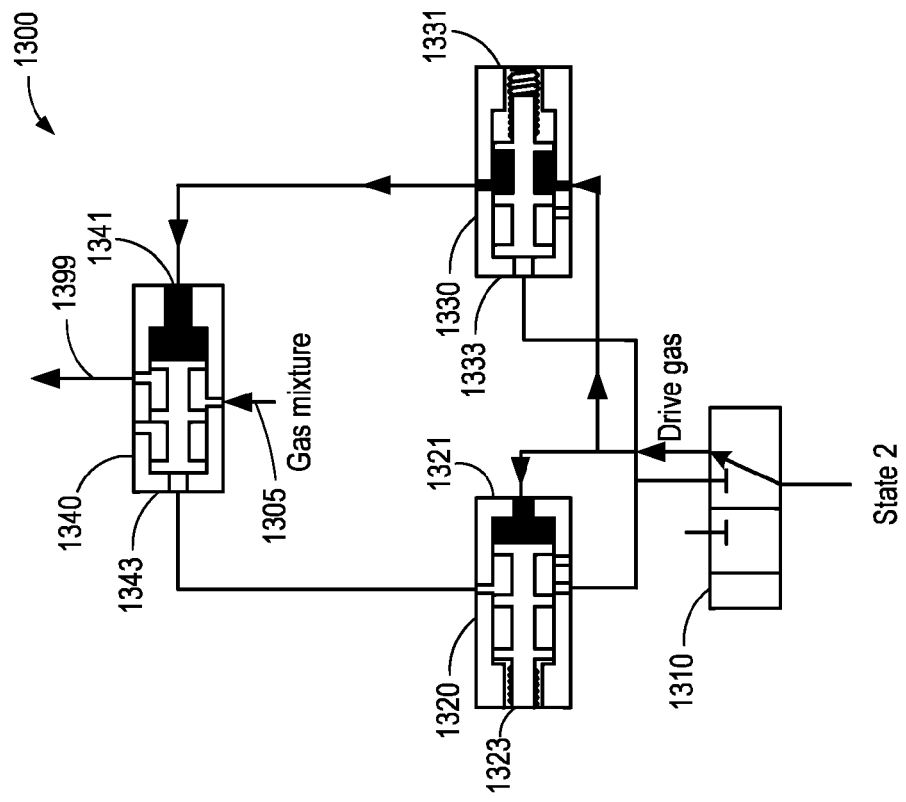
FIG. 13B illustrates a diagram of a network of shuttle valves and a three-way selector valve directing a gas mixture to an ACGO instead of a primary breathing system.
Figure 13A:
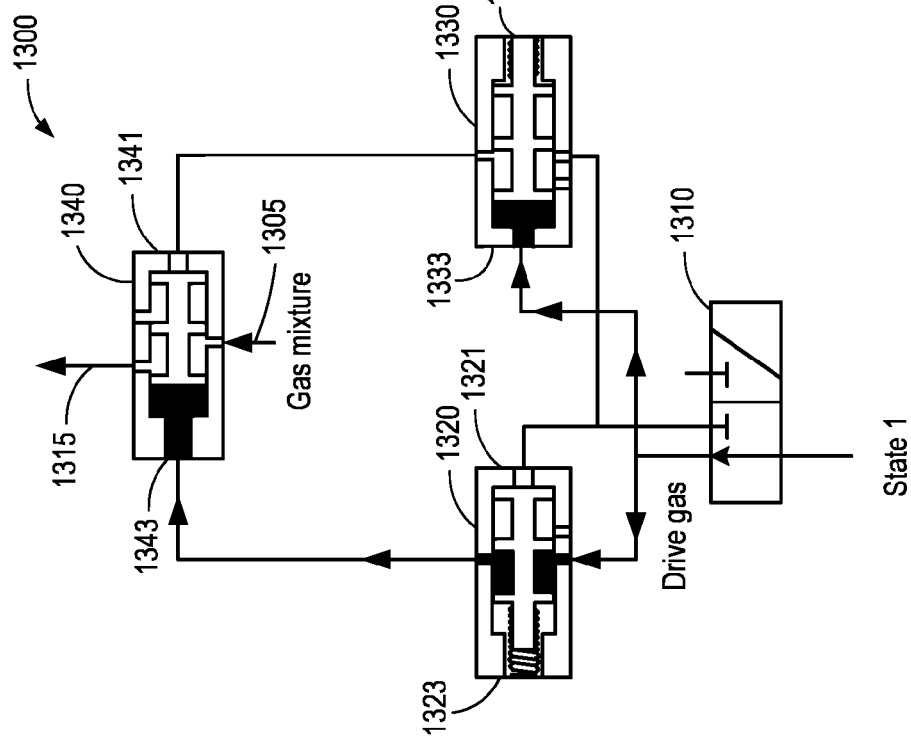
FIG. 13A illustrates a diagram of a network of shuttle valves and a three-way selector valve directing a gas mixture to a primary breathing system instead of an ACGO.

FIG. 13A illustrates a diagram 1300 of a network of shuttle valves 1320, 1330, and 1340 and a three-way selector valve 1310 directing a gas mixture 1305 to a primary breathing system 1315 instead of an ACGO 1399 (FIG. 13B). As illustrated, a first shuttle valve 1320 may be biased by a resilient member, e.g., a spring, on a left side 1323, such that a gas may be passed through the first shuttle valve 1320 in a default position. Similarly, a second shuttle valve 1330 may be biased by a resilient member on a right side 1331, such that a gas may be passed through the second shuttle valve 1330 in a default position.

A three-way selector valve 1310 may be toggled between a first state and a second state. In a first state, illustrated in FIG. 13A, the three-way selector valve may direct a drive gas along the line of arrows through the first shuttle valve 1320. The drive gas may also be directed into a left side 1333 of the second shuttle valve 1330 in the first state. Accordingly, in the first state, the drive gas may be passed through the first shuttle valve 1320 and not through the second shuttle valve 1330.

In the first state, the drive gas that flows through the first shuttle valve 1320 may enter a left side 1343 of a third shuttle valve 1340. The drive gas may cause a piston within the third shuttle valve 1340 to translate to a first position. With the third shuttle valve 1340 in the first position, the gas mixture 1305 may flow through the third shuttle valve 1340 to the primary breathing system 1315.

The three-way selector valve 1310 may be electronically toggled to a second state. As illustrated in FIG. 13B, in the second state, the drive gas may be allowed to flow through the second shuttle valve 1330 in the default position. The drive gas may also flow into a right side 1321 of the first shuttle valve 1320, causing its internal piston to translate against its spring. Accordingly, in the second state, the drive gas may be passed through the second shuttle valve 1330 and not through the first shuttle valve 1320.

In the second state, the drive gas that flows through the second shuttle valve 1330 may enter a right side 1341 of the third shuttle valve 1340. The drive gas may cause a piston within the third shuttle valve 1340 to translate to a second position. With the third shuttle valve 1340 in the second position, the gas mixture 1305 may flow through the third shuttle valve 1340 to an ACGO 1399.

Accordingly, by comparing FIGS. 13A and 13B, it can be seen that the gas mixture 1305 can be electronically diverted through either the primary breathing system 315 or the ACGO 1399, depending on the state of the three-way selector valve 1310. The state of the three-way selector valve 1310 may be toggled by an electronic input. The electronic input may be generated by a controller automatically or in response to a user selection. For example, a user may electronically select either the ACGO 1399 or the primary breathing machine 1315 via an electronic input, such as a button, switch, toggle, slider, touch pad, touch screen, voice command, gesture, etc.

Figure 14:
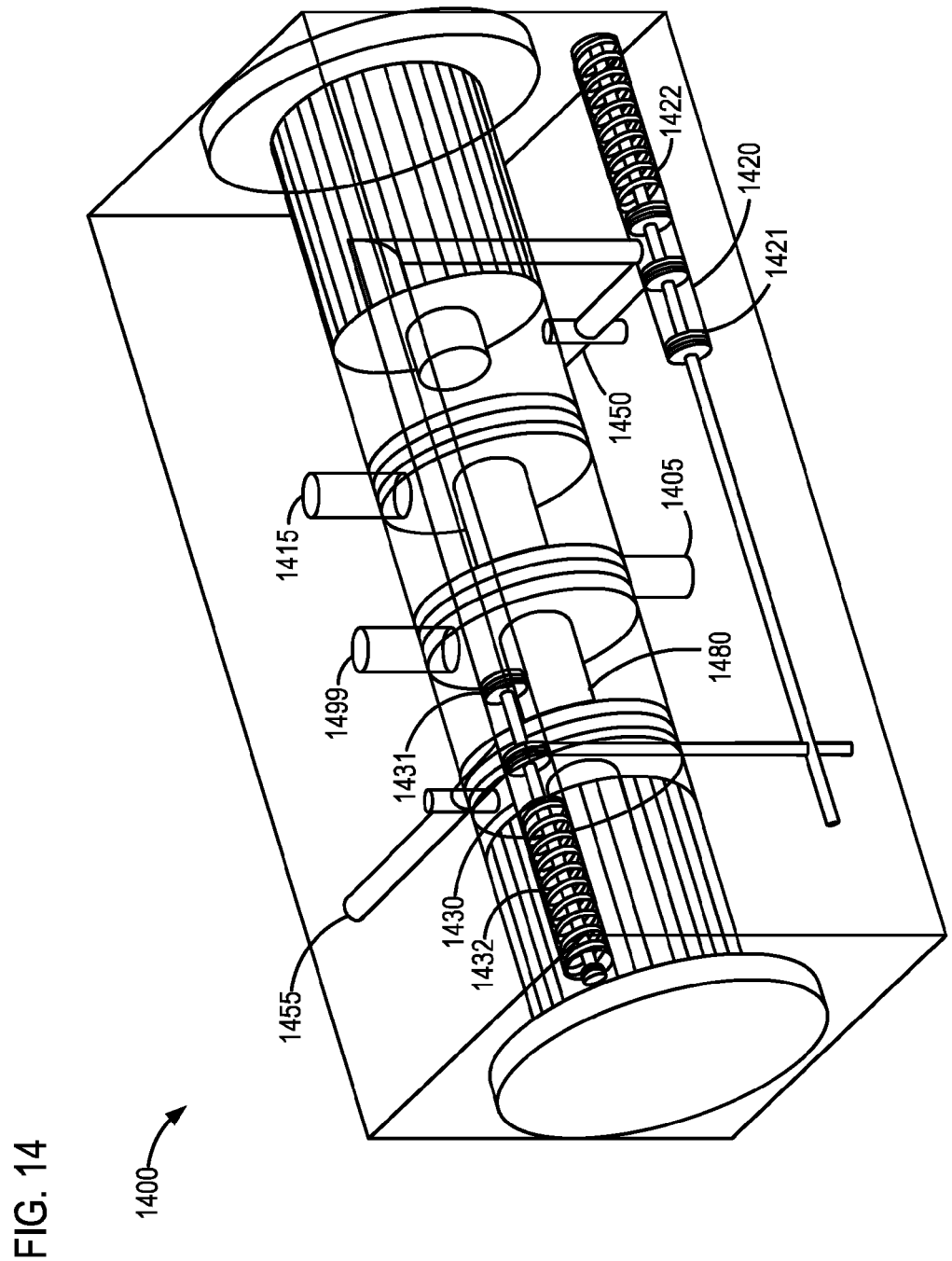
FIG. 14 illustrates a multi-channel manifold for selectively directing a gas mixture between a primary breathing system and an ACGO.

FIG. 14 illustrates a multi-channel manifold 1400 for selectively directing a gas mixture between a primary breathing system 1415 and an ACGO 1499. The multi-channel manifold 1400 may be configured to perform the functions described in conjunction with the diagrams of FIGS. 13A and 13B. Accordingly, an electronic signal may be generated to cause a drive gas to be directed to either a first drive gas inlet 1450 or a second drive gas inlet 1455. In a first state, a drive gas may be directed through the first drive gas inlet 1450. The drive gas may bias a master piston 1480 to a first position (the left, as illustrated). In the first position, a gas mixture from inlet 1405 may be directed through a first valve channel to an outlet for the primary breathing system 1415. The drive gas may also be directed through a first shuttle valve 1420 and cause a piston 1431 in a second shuttle valve 1430 to compress against a bias spring 1432.

In a second state, the drive gas may be directed through the second drive gas inlet 1455. The drive gas may bias the master piston 1480 to a second position (the right, opposite of the illustration). In the second position, the gas mixture from the inlet 1405 may be directed through a second valve channel to the ACGO 1499. The drive gas may also be directed through a second shuttle valve 1430 to cause a piston 1421 in the first shuttle valve 1420 to compress against a bias spring 1422.

Figure 15A:
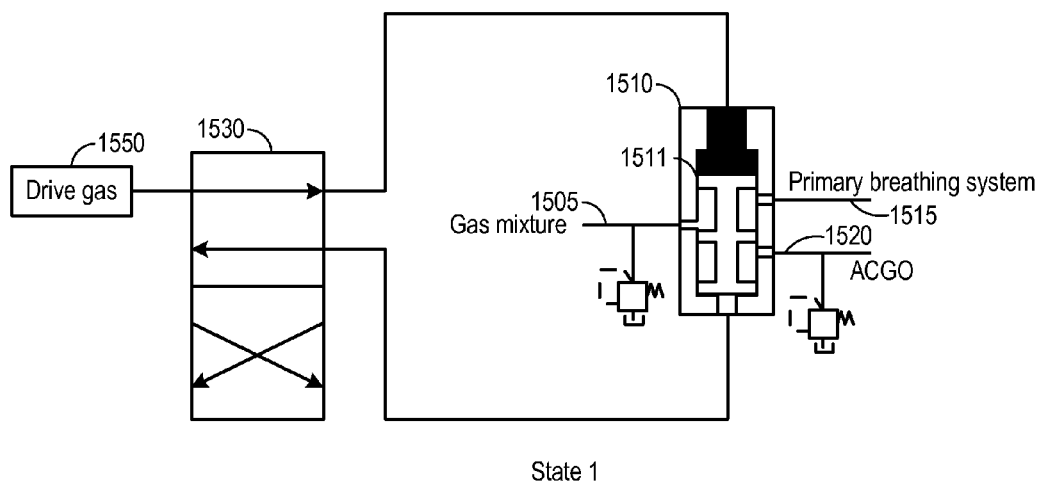
FIG. 15A illustrates a diagram of a system including a four-way selector valve and a piloted shuttle valve in a first state, such that a gas mixture is directed to a primary breathing system.

Accordingly, by selectively directing a drive gas through one of the first 1450 and second 1455 drive inlets, a master piston 1480 may be toggled between two positions. Depending on the position of the master piston 1480, the gas mixture from the inlet 1405 may be directed to the primary breathing machine 1415 or the ACGO 1499. An electronic valve may be used to selectively divert a drive gas into either the first 1450 or the second 1455 drive inlets. Accordingly, any type of electronic interface or controller may be used to selectively direct a gas mixture to either the primary breathing machine 1415 or the ACGO 1499. FIG. 15A illustrates a diagram of a system including a four-way selector valve 1530 and a piloted shuttle valve 1510 in a first state, such that a gas mixture 1505 is directed to a primary breathing system 1515. As illustrated, the piloted shuttle valve 1510 may include an internal piston 1511 configured to translate between a first position (shown in FIG. 15A) and a second position (shown in FIG. 15B). To divert the gas mixture 1505 to the primary breathing system 1515, an electronically controlled four-way selector valve 1530 may cause the drive gas 1550 to flow to a first drive gas inlet on the piloted shuttle valve 1510. The four-way selector valve 1530 may prevent the drive gas 1550 from flowing to a second drive gas inlet on the piloted shuttle valve 1510. Accordingly, the drive gas 1550 may cause the piston 1511 to translate to a first position, in which the gas mixture 1505 flows through a piston channel to the primary breathing system 1515.

Figure 15B:
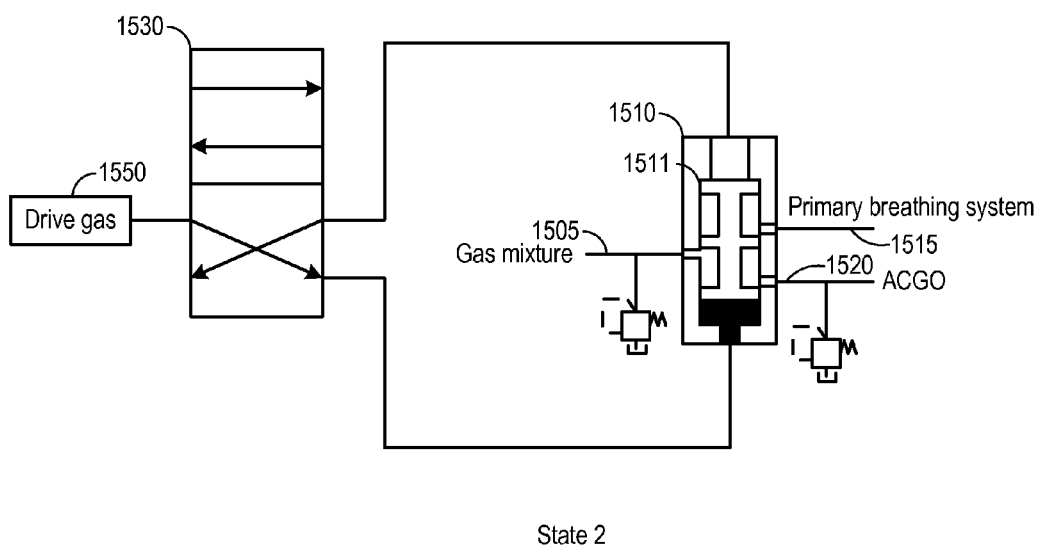
FIG. 15B illustrates a diagram of the system of FIG. 15A system in a second state, such that a gas mixture is directed to an ACGO.

FIG. 15B illustrates a diagram of the system of FIG. 15A system in a second state, such that the gas mixture 1505 is directed to an ACGO 1520. To divert the gas mixture 1505 to the ACGO 1520, the four-way selector valve 1530 may prevent the drive gas 1550 from flowing to the first drive gas inlet on the piloted shuttle valve 1510. The four-way selector valve 1530 may allow the drive gas 1550 to flow to the second drive gas inlet on the piloted shuttle valve 1510. The drive gas 1550 may cause the piston 1511 to translate to a second position, in which the gas mixture 1505 flows through a second piston channel to the ACGO 1520.

As illustrated, the first piston channel may be connected to the primary breathing system 1515, and the second piston channel may be connected to the ACGO 1520. By translating the piston 1511 between a first and second position, the gas mixture 1505 input may be toggled between the first and second piston channels. The piston 1511 may prevent the first and second channels from connecting. Accordingly, the primary breathing system 1515 and the ACGO 1520 may remain independent from one another.

Comparing FIGS. 15A and 15B, it can be seen that by electronically toggling the four-way selector valve 1530, the gas mixture 1505 can be diverted to either the primary breathing system 1515 or the ACGO 1520. The four-way selector valve 1530 may be controlled by an electronic interface and/or a backup manual interface. The illustrated configuration allows an ACGO valve (as described in FIGS. 1, 2, and 5) to be electronically controlled via selector valves while the piloted shuttle valve 1510 accommodates relatively high flow rates of the gas mixture and/or anesthetics, provides biocompatibility, operates in an oxygen-rich environment, and/or conveys potentially corrosive anesthetic agents.

Figure 16A:
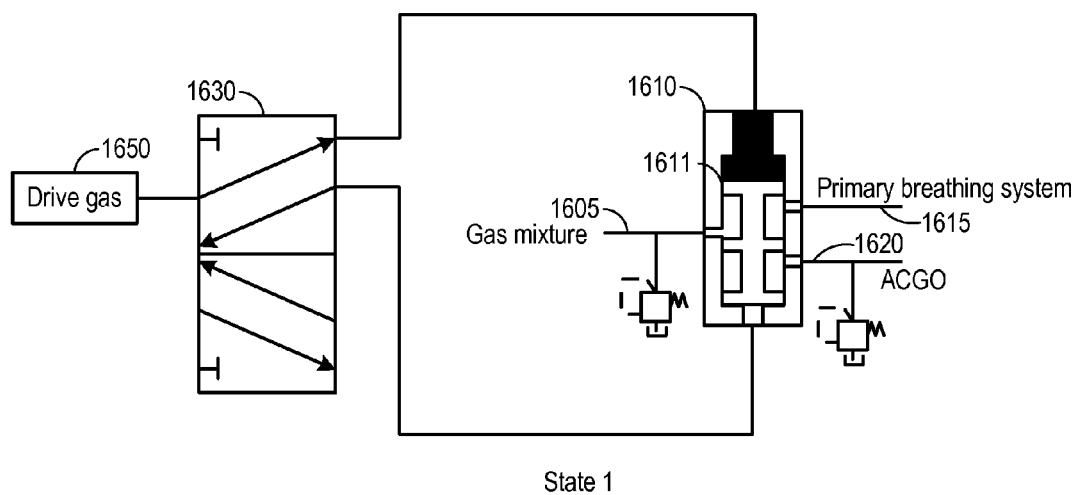
FIG. 16A illustrates a diagram of a system including a latching four-way selector valve and a piloted shuttle valve in a first state, such that a gas mixture is directed to a primary breathing system.

FIG. 16A illustrates a diagram of a system including a latching four-way selector valve 1630 and a piloted shuttle valve 1610 in a first state, such that a gas mixture 1605 is directed to a primary breathing system 1615. FIG. 16A is similar to FIG. 15A, except that a four port, latching four-way selector valve 1630 is depicted in place of the five port, four-way selector valve 1530. As illustrated, the piloted shuttle valve 1610 may include an internal piston 1611 configured to translate between a first position (shown in FIG. 16A) and a second position (shown in FIG. 16B). To divert the gas mixture 1605 to the primary breathing system 1615, an electronically controlled latching four-way selector valve 1630 may cause the drive gas 1650 to flow to a first drive gas inlet on the piloted shuttle valve 1610. The latching four-way selector valve 1630 may prevent the drive gas 1650 from flowing to a second drive gas inlet on the piloted shuttle valve 1610. Accordingly, the drive gas 1650 may cause the piston 1611 to translate to a first position, in which the gas mixture 1605 flows through a piston channel to the primary breathing system 1615.

Figure 16B:
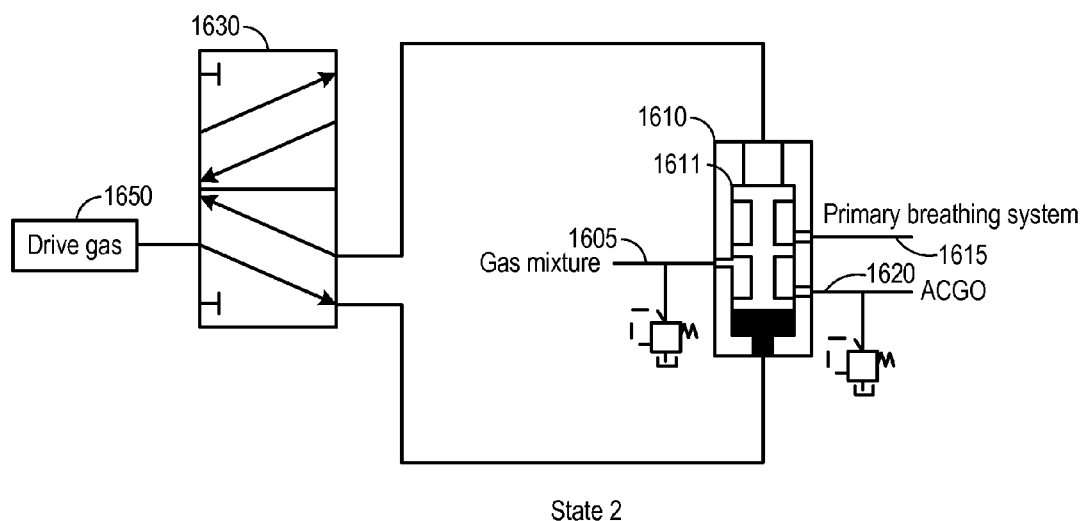
FIG. 16B illustrates a diagram of the system of FIG. 16A system in a second state, such that a gas mixture is directed to an ACGO.

FIG. 16B illustrates a diagram of the system of FIG. 16A system in a second state, such that a gas mixture 1605 is directed to an ACGO 1620. FIG. 16B is similar to FIG. 15B, except that a four port, latching four-way selector valve 1630 is depicted in place of the five port, four-way selector valve 1530. To divert the gas mixture 1605 to the ACGO 1620, the latching four-way selector valve 1630 may prevent the drive gas 1650 from flowing to the first drive gas inlet on the piloted shuttle valve 1610. The latching four-way selector valve 1630 may allow the drive gas 1650 to flow to the second drive gas inlet on the piloted shuttle valve 1610. The drive gas 1650 may cause the piston 1611 to translate to a second position, in which the gas mixture 1605 flows through a second piston channel to the ACGO 1620.

As illustrated, the first piston channel may be connected to the primary breathing system 1615, and the second piston channel may be connected to the ACGO 1620. By translating the piston 1611 between a first and second position, the gas mixture 1605 input may be toggled between the first and second piston channels. The piston 1611 may prevent the first and second channels from connecting. Accordingly, the primary breathing system 1615 and the ACGO 1620 may remain independent from one another.

Again, the illustrated configuration may accommodate relatively high flow rates of the gas mixture and/or anesthetics, provides biocompatibility, operates in an oxygen-rich environment, and/or conveys potentially corrosive anesthetic agents, while simultaneously allow for electronic switching between a primary breathing system 1615 and an ACGO 1620.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient. It will be appreciated that a piloted shuttle valve for selectively diverting an input fluid to one of two outputs may be utilized in various contexts and in conjunction with any of a wide variety of fluids and/or fluid systems.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. An anesthesia delivery apparatus including system for controlling a flow rate of a plurality of fluids with a manual mode and an electronic mode, the system comprising:
    a plurality of manual valves, each manual valve receives a respective fluid of the plurality of fluids;
    a plurality of electronically controlled valves, each electronically controlled valve receives the respective fluid of the plurality of fluids:
    a plurality of manual mode valves that open in the manual mode so a respective fluid flows to the manual valves and that close in the electronic mode so the respective fluid does not flow to the manual valves:
    a plurality of electronic mode valves that open in the electronic mode so the respective fluid flows to the electronically controlled valves and that close in the manual mode so the respective fluid does not flow to the electronically controlled valves;
    multiple manually settable valve actuators, each actuator operably connected to one of the plurality of manual valves and one of the plurality of electronically controlled valves for independently controlling the flow rate of each of the plurality of fluids;
    a plurality of encoders, each encoder configured to electronically encode a flow rate selection from a respective actuator during the electronic mode;
    a controller configured to receive the encoded flow rate during the electronic mode and control the respective electronically controlled valve to pass the respective fluid based on the flow rate received from the respective encoder;
    a piloted shuttle valve, the piloted shuttle valve comprising:
        a piston including a first channel and a second channel, the piston configured to be translated between at least a first position and a second position by a drive-fluid;
        an input configured to receive one or more fluids of the plurality of fluids from either the plurality of manual valves in the manual mode or the plurality of electronically controlled valves in the electronic mode, the input in fluid communication with the first channel when the piston is in the first position and the input in fluid communication with the second channel when the piston is in the second position;
        a first output in fluid communication with the first channel, such that when the piston is in the first position, one or more fluids of the plurality of fluids flow from the input to the first output; and
        a second output in fluid communication with the second channel, such that when the piston is in the second position, one or more fluids of the plurality of fluids flow from the input to the second output; and
    an electronically controlled valve system configured to direct the drive-fluid for selectively translating the piston between at least the first position and the second position.

2. The apparatus of claim 1, wherein the one or more fluids comprises one or more gases.

3. The apparatus of claim 2, wherein one or more fluids further comprises one or more anesthetic agents.

4. The apparatus of claim 1, wherein the drive-fluid comprises one or more gases.

5. The apparatus of claim 1, wherein the input is configured to receive one or more gases from an anesthetic delivery system, wherein the first output is configured to selectively deliver the one or more gases from the anesthetic delivery system to a primary breathing system of the anesthetic delivery system, and wherein the second output is configured to selectively deliver the one or more gases from the anesthetic delivery system to an auxiliary common gas outlet (ACGO).

6. The apparatus of claim 1, wherein the piloted shuttle valve further comprises a position detection switch configured to detect when the piston is in one of the first position and the second position.

7. The apparatus of claim 6, wherein the piloted shuttle valve further comprises a guard configured to physically protect the position detection switch.

8. The apparatus of claim 1, wherein the piloted shuttle valve further comprises a pressure relief valve fluidly connected to the input.

9. The apparatus of claim 1, wherein the piloted shuttle valve further comprises a pressure relief valve fluidly connected to the first channel.

10. The apparatus of claim 1, wherein the piloted shuttle valve further comprises a pressure relief valve fluidly connected to the second channel.

11. The apparatus of claim 1, wherein the piloted shuttle valve further comprises:
a resilient member configured to bias the piston to the first position, such that the one of more fluids of the plurality of fluids is configured to flow from the input to the first output; and
a drive-fluid inlet configured to receive the drive-fluid directed by the electronically controlled valve system, such that the drive-fluid selectively causes the piston to translate to the second position overcoming the bias of the resilient member.

12. The apparatus of claim 11, wherein the resilient member comprises a spring.

13. The apparatus of claim 1, further comprising:
a first drive-fluid inlet configured to receive the drive-fluid directed by the electronically controlled valve system and cause the piston to translate to the first position within the piloted shuttle valve; and
a second drive fluid inlet configured to receive the drive-fluid directed by the electronically controlled valve system and cause the piston to translate to the second position within the piloted shuttle valve, and
wherein the electronically controlled valve system is configured to be electronically controlled to selectively direct the drive-fluid into the first drive-fluid inlet and the second drive-fluid inlet.

14. An anesthesia delivery apparatus including an electronic system for controlling the flow rate of a fluid, the electronic system for controlling the flow rate of the fluid comprising:
a piloted shuttle valve, the piloted shuttle valve comprising:
a piston including a first channel and a second channel, the piston configured to be translated between at least a first position and a second position by a drive-fluid;
a first drive-fluid inlet configured to receive the drive-fluid to translate the piston to the first position;
a second drive-fluid inlet configured to receive the drive-fluid to translate the piston to the second position;
an input configured to receive the fluid, the input in fluid communication with the first channel when the piston is in the first position and the input in fluid communication with the second channel when the piston is in the second position;
a first output in fluid communication with the first channel, such that when the piston is in the first position, the fluid flows from the input to the first output and
a second output in fluid communication with the second channel, such that when the piston is in the second position, the fluid flows from the input to the second output and
an electronically controlled valve system configured to direct the drive-fluid to the first drive-fluid inlet of the piloted shuttle valve or the second drive-fluid inlet of the piloted shuttle valve for selectively translating the piston between at least the first position and the second position, comprising:
a first biased shuttle valve comprising:
a piston including a first channel and a second channel, the piston configured to be translated between a first position and a second position;
a resilient member configured to bias the piston to the first position;
an input configured to receive the drive-fluid, the input aligned with the first channel when the piston is in the first position and the input aligned with the second channel when the piston is in the second position;
an output aligned with the first channel when the piston is in the first position and aligned with the second channel with the piston is in the second position; and
a drive-fluid inlet configured to selectively receive the drive-fluid, such that the drive-fluid received via the drive-fluid inlet causes the piston to translate to the second position overcoming the bias of the resilient member;
a second biased shuttle valve comprising:
a piston including a first channel and a second channel, the piston configured to be translated between a first position and a second position;
a resilient member configured to bias the piston to the first position;
an input configured to receive the drive-fluid, the input aligned with the first channel when the piston is in the first position and the input aligned with the second channel when the piston is in the second position;
an output aligned with the first channel when the piston is in the first position and aligned with the second channel when the piston is in the second position; and
a drive-fluid inlet configured to selectively receive the drive-fluid, such that the drive-fluid received via the drive-fluid inlet causes the piston to translate to the second position overcoming the bias of the resilient member; and
a three-way selector valve configured to be electronically toggled, such that:
in a first state:
the drive-fluid is configured to flow from the input of the first biased shuttle valve through the output of the first biased shuttle valve to the first drive-fluid inlet of the piloted shuttle valve; and
the drive-fluid is configured to flow into the drive-fluid inlet of the second biased shuttle valve, causing the piston of the second biased shuttle valve to translate to the second state; and in a second state:
the drive-fluid is configured to flow from the input of the second biased shuttle valve through the output of the second biased shuttle valve to the second drive-fluid inlet of the piloted shuttle valve; and the drive-fluid is configured to flow into the drive-fluid inlet of the first biased shuttle valve, causing the piston of the first biased shuttle valve to translate to the second state.

15. The apparatus of claim 14, wherein the piloted shuttle valve, the first biased shuttle valve, and the second biased shuttle valve are integrated into a single manifold, the single manifold comprising:

a first drive-fluid inlet connected to the input of the first biased shuttle valve and the drive-fluid inlet of the second biased shuttle valve;

a second drive-fluid inlet connected to the input of the second biased shuttle valve and the drive-fluid inlet of the first biased shuttle valve;

a fluid input connected to the input of piloted shuttle valve;

a first fluid output connected to the first output of the piloted shuttle valve; and a second fluid output connected to the second output of the piloted shuttle valve, wherein the output of the first biased shuttle valve is internally connected to the first drive-fluid inlet of the piloted shuttle valve, and wherein the output of the second biased shuttle valve is internally connected to the second drive-fluid inlet of the piloted shuttle valve.

16. A method for controlling a flow rate of a plurality of fluids during a manual mode and an electronic mode, comprising:

during the manual mode opening a respective manual mode valve of a plurality of manual mode valves to connect a respective fluid of the plurality of fluids to a respective manual valve of a plurality of manual valves and closing a respective electronic mode valve to disconnect the respective fluid of the plurality of fluids from a respective electronically controlled valve of a plurality of electronically controlled valves;

during the electronic mode opening the respective electronic mode valve of the plurality of electronic mode valves to connect the respective fluid of the plurality of fluids to the respective electronically controlled valve of the plurality of electronically controlled valves and closing the respective manual mode valve to disconnect the respective fluid of the plurality of fluids from the respective manual valve;

receiving, at an input of a piloted shuttle valve, one or more fluids from the manual valves in the manual mode or the electronically controlled valves in the electronic mode;

directing the one or more fluids of the plurality of fluids from the input of the piloted shuttle valve to a first output of the piloted shuttle valve via a first channel in a piston of the piloted shuttle valve, with the piston in a first position within the piloted shuttle valve;

electronically actuating a valve system to cause a drive-fluid to move the piston of the piloted shuttle valve from the first position to a second position, where the input is aligned with the first channel when the piston is in the first position and the input is aligned with a second channel in the piston when the piston is in the second position; and directing the one or more fluids of the plurality of fluids from the input to a second output of the piloted shuttle valve via the second channel with the piston in the second position.

17. The method of claim 16, wherein the one or more fluids comprises one or more gases.

18. The method of claim 17, wherein the one or more fluids further comprises one or more anesthetic agents.

19. The method of claim 17, wherein the drive-fluid comprises one or more gases.

20. The method of claim 16, wherein the input is configured to receive one or more gases from an anesthetic delivery system, wherein the first output is configured to selectively deliver the one or more gases from the anesthetic delivery system to a primary breathing system of the anesthetic delivery system, and wherein the second output is configured to selectively deliver the one or more gases from the anesthetic delivery system to an auxiliary common gas outlet (ACGO).

21. The method of claim 16, further comprising:
detecting when the piston is in one of the first position and the second position using a position detection switch.

22. The method of claim 16, further comprising
biasing the piston to the first position via a resilient member, such that the one or more fluids is configured to flow from the input to the first output in the biased first position; and receiving the drive-fluid directed by the electronically controlled valve system via a drive-fluid inlet, such that the drive-fluid causes the piston to translate to the second position overcoming the bias of the resilient member.

23. The method of claim 22, wherein the resilient member comprises a spring.

24. The method of claim 16, wherein electronically actuating a valve system to cause the drive-fluid to move the piston of the piloted shuttle valve from the first position to the second position comprises:

directing the drive fluid into a first drive-fluid inlet to cause the piston to translate to the first position within the piloted shuttle valve; and directing the drive fluid into a second drive-fluid inlet to cause the piston to translate to the second position within the piloted shuttle valve.

* * * * *